(12) United States Patent
Gremyachinskiy et al.

(10) Patent No.: US 10,669,580 B2
(45) Date of Patent: Jun. 2, 2020

(54) TAGGED NUCLEOTIDES USEFUL FOR NANOPORE DETECTION

(71) Applicant: Roche Sequencing Solutions, Inc., Pleasanton, CA (US)

(72) Inventors: Dmitriy Gremyachinskiy, San Francisco, CA (US); Peter Crisalli, Sunnyvale, CA (US); Andrew Trans, Mountain View, CA (US); Ashwini Bhat, Milpitas, CA (US)

(73) Assignee: Roche Sequencing Solutions, Inc., Pleasanton, CA (US)

(*) Notice: Subject to any disclaimer, the term of this patent is extended or adjusted under 35 U.S.C. 154(b) by 192 days.

(21) Appl. No.: 15/684,726

(22) Filed: Aug. 23, 2017

(65) Prior Publication Data

US 2018/0057870 A1  Mar. 1, 2018

Related U.S. Application Data

(60) Provisional application No. 62/380,059, filed on Aug. 26, 2016.

(51) Int. Cl.
| | | |
|---|---|---|
| *C12Q 1/68* | (2018.01) | |
| *C07H 19/04* | (2006.01) | |
| *C07H 19/10* | (2006.01) | |
| *C07H 21/04* | (2006.01) | |
| *C12Q 1/6869* | (2018.01) | |
| *C12Q 1/6823* | (2018.01) | |
| *C07H 19/06* | (2006.01) | |
| *C07K 14/00* | (2006.01) | |

(52) U.S. Cl.
CPC .......... *C12Q 1/6869* (2013.01); *C07H 19/06* (2013.01); *C07H 19/10* (2013.01); *C07H 21/04* (2013.01); *C07K 14/00* (2013.01); *C12Q 1/6823* (2013.01)

(58) Field of Classification Search
CPC ...... C12Q 1/6869; C07H 19/04; C07H 19/10; C07H 21/04
USPC ............................... 536/4.1, 23.1, 24.1, 26.6
See application file for complete search history.

(56) References Cited

U.S. PATENT DOCUMENTS

| | | | |
|---|---|---|---|
| 5,795,782 A | 8/1998 | Church et al. | |
| 6,015,714 A | 1/2000 | Baldarelli et al. | |
| 6,267,872 B1 | 7/2001 | Akeson et al. | |
| 6,362,002 B1 | 3/2002 | Denison et al. | |
| 6,464,842 B1 | 10/2002 | Golovchenko et al. | |
| 6,617,113 B2 | 9/2003 | Deamer | |
| 6,627,067 B1 | 9/2003 | Branton et al. | |
| 6,673,615 B2 | 1/2004 | Denison et al. | |
| 6,746,594 B2 | 6/2004 | Akeson et al. | |
| 7,005,264 B2 | 2/2006 | Su et al. | |
| 7,846,738 B2 | 12/2010 | Golovchenko et al. | |
| 2003/0044781 A1 | 3/2003 | Korlach et al. | |
| 2003/0104428 A1 | 6/2003 | Branton et al. | |
| 2003/0124576 A1 | 6/2003 | Branton et al. | |
| 2004/0121525 A1 | 6/2004 | Chopra et al. | |
| 2009/0298072 A1 | 12/2009 | Ju et al. | |
| 2013/0244340 A1 | 9/2013 | Davis et al. | |
| 2013/0264207 A1 | 10/2013 | Ju et al. | |
| 2014/0134616 A1 | 5/2014 | Davis et al. | |
| 2014/0309144 A1* | 10/2014 | Turner ................. G01N 27/447 506/16 |
| 2015/0119259 A1 | 4/2015 | Ju et al. | |
| 2015/0368710 A1 | 12/2015 | Fuller et al. | |
| 2016/0333327 A1 | 11/2016 | Ayer et al. | |
| 2017/0088588 A1 | 3/2017 | Dorwart et al. | |
| 2017/0088890 A1 | 3/2017 | Craig et al. | |
| 2017/0175183 A1 | 6/2017 | Ju et al. | |
| 2017/0306397 A1 | 10/2017 | Craig et al. | |
| 2017/0342485 A1 | 11/2017 | Gremyachinskiy et al. | |
| 2018/0002750 A1 | 1/2018 | Ambroso et al. | |

FOREIGN PATENT DOCUMENTS

| | | |
|---|---|---|
| WO | 2005111240 | 11/2005 |
| WO | 2013191793 A | 4/2013 |
| WO | 2013154999 A | 10/2013 |
| WO | 2015148402 A | 10/2015 |
| WO | 2017024049 | 2/2017 |
| WO | 2017042038 A | 3/2017 |
| WO | 2018026855 | 2/2018 |

OTHER PUBLICATIONS

PCT International Search Report and Written Opinion of the International Searching Authority in PCT/EP2017/071379 (dated Nov. 15, 2017).
Fuller et al. (2016) "Real-time single-molecule electronic DNA sequencing by synthesis using polymer-tagged nucleotides on a nanopore array," Proc. Nat'l. Acad. Sci. USA, vol. 113(19): 5233-5238.
Kumar et al., (2012) "PEG-Labeled Nucleotides and Nanopore Detection for Single Molecule DNA Sequencing by Synthesis," Scientific Reports, 2:684; DOI: 10.1038/srep00684.
Robertson et al. (2007) "Single-molecule mass spectrometry in solution using a solitary nanopore," Proc. Nat'l. Acad. Sci. USA, 104; 8207.
Shchepinov et al., (1997) "Oligonucleotide dendrimers: synthesis and use as polylabelled DNA probes," Nucleic Acids Research, vol. 25, No. 22, 4447-4454.

(Continued)

*Primary Examiner* — Jezia Riley
(74) *Attorney, Agent, or Firm* — FisherBroyles, LLP; Adam K. Whiting

(57) ABSTRACT

The present disclosure relates to compounds comprising a negatively-charged polymer moiety which is capable of entering a nanopore and upon entering a nanopore in the presence of positive ions results in an increased flow of the positive ions through the nanopore. The present disclosure provides methods of preparing the compounds and for their use as nanopore-detectable tags, in particular, for nanopore-based nucleic acid detection and sequencing.

12 Claims, 1 Drawing Sheet
Specification includes a Sequence Listing.

(56) References Cited

OTHER PUBLICATIONS

Valeva et al. (2001) "Membrane insertion of the heptameric staphylococcal alpha-toxin pore—A domino-like structural transition that is allosterically modulated by the target cell membrane," J. Biol. Chem. 276(18): 14835-14841.

Zakeri and Howarth (2010) "Spontaneous Intermolecular Amide Bond Formation between Side Chains for Irreversible Peptide Targeting," J. Am. Chem. Soc. 132:4526-7.

* cited by examiner

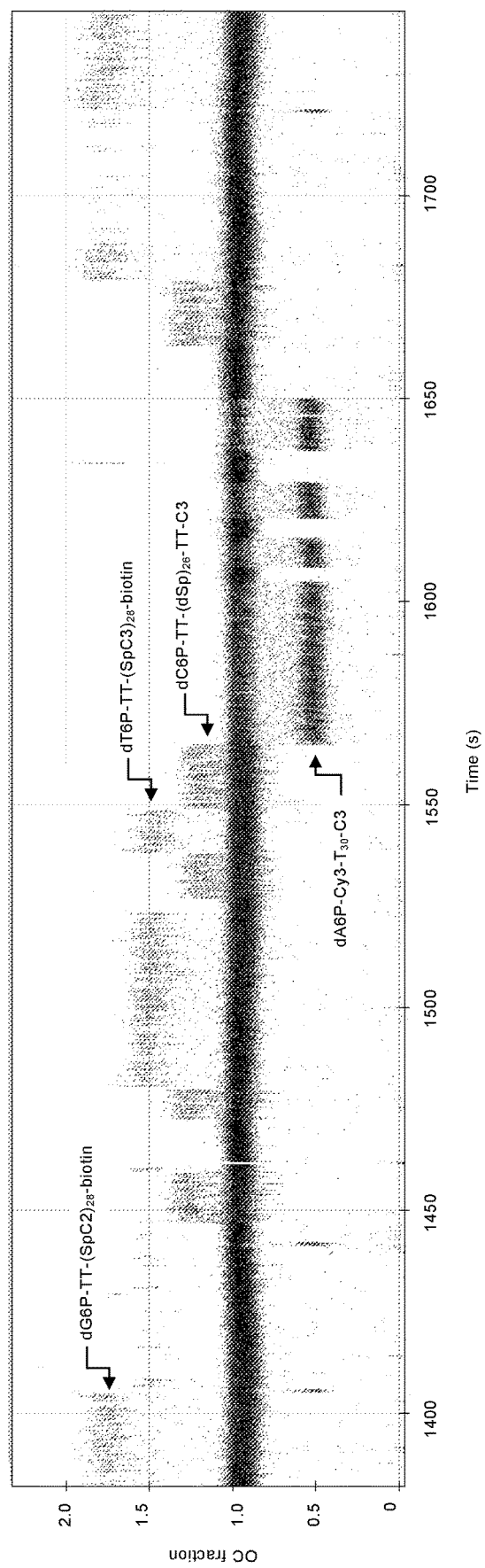

SEQUENCE LISTING

<160> NUMBER OF SEQ ID NOS: 22

<210> SEQ ID NO 1
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (3)..(30)
<223> OTHER INFORMATION: ethyl amidite

<400> SEQUENCE: 1
ttnnnnnnnn nnnnnnnnnn nnnnnnnnnn                                    30

<210> SEQ ID NO 2
<211> LENGTH: 30
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (3)..(30)

```
<223> OTHER INFORMATION: propyl amidite

<400> SEQUENCE: 2
ttnnnnnnnn nnnnnnnnnn nnnnnnnnnn                                    30

<210> SEQ ID NO 3
<211> LENGTH: 31
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(31)
<223> OTHER INFORMATION: propyl amidite

<400> SEQUENCE: 3
nnnnnnnnnn nnnnnnnnnn nnnnnnnnnn n                                  31

<210> SEQ ID NO 4
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (3)..(28)
<223> OTHER INFORMATION: furan amidite

<400> SEQUENCE: 4
ttnnnnnnnn nnnnnnnnnn nnnnnnnntt                                    30

<210> SEQ ID NO 5
<211> LENGTH: 30
<212> TYPE: DNA
<213> ORGANISM: Artificial sequence
<220> FEATURE:
<223> OTHER INFORMATION: synthesized oligonucleotide
<220> FEATURE:
<221> NAME/KEY: misc_feature
<222> LOCATION: (3)..(30)
<223> OTHER INFORMATION: 2,2,3,3-tetrafluorobutyl amidite

<400> SEQUENCE: 5
ttnnnnnnnn nnnnnnnnnn nnnnnnnnnn                                    30

<210> SEQ ID NO 6
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (3)..(30)
<223> OTHER INFORMATION: hepta-2,4-diyn amidite

<400> SEQUENCE: 6
ttnnnnnnnn nnnnnnnnnn nnnnnnnnnn                                    30

<210> SEQ ID NO 7
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
```

```
<222> LOCATION: (3)..(28)
<223> OTHER INFORMATION: furan amidite
<220> FEATURE:
<221> NAME/KEY: misc_feature
<222> LOCATION: (30)..(30)
<223> OTHER INFORMATION: T-propanol

<400> SEQUENCE: 7
ttnnnnnnnn nnnnnnnnnn nnnnnnnntt                                    30

<210> SEQ ID NO 8
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (3)..(30)
<223> OTHER INFORMATION: ethyl amidite
<220> FEATURE:
<221> NAME/KEY: misc_feature
<222> LOCATION: (30)..(30)
<223> OTHER INFORMATION: 3'-biotin

<400> SEQUENCE: 8
ttnnnnnnnn nnnnnnnnnn nnnnnnnnnn                                    30

<210> SEQ ID NO 9
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (3)..(30)
<223> OTHER INFORMATION: propyl amidite
<220> FEATURE:
<221> NAME/KEY: misc_feature
<222> LOCATION: (30)..(30)
<223> OTHER INFORMATION: 3' biotin

<400> SEQUENCE: 9
ttnnnnnnnn nnnnnnnnnn nnnnnnnnnn                                    30

<210> SEQ ID NO 10
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (30)..(30)
<223> OTHER INFORMATION: T-propanol

<400> SEQUENCE: 10
tttttttttt tttttttttt tttttttttt                                    30

<210> SEQ ID NO 11
<211> LENGTH: 90
<212> TYPE: DNA
<213> ORGANISM: Artificial Sequence
<220> FEATURE:
<223> OTHER INFORMATION: Synthesized oligonucleotide

<400> SEQUENCE: 11
cagtcagtag agagagatat ctctctcaaa aacggaggag gaggacagtc agtagagaga    60
```
gatatctctc tcaaaaacgg aggaggagga                                        90

<210> SEQ ID NO 12
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(8)
<223> OTHER INFORMATION: ethyl amidite
<220> FEATURE:
<221> NAME/KEY: misc_feature
<222> LOCATION: (15)..(30)
<223> OTHER INFORMATION: ethyl amidite

<400> SEQUENCE: 12
nnnnnnnntt ttttnnnnnn nnnnnnnnnn                                        30

<210> SEQ ID NO 13
<211> LENGTH: 30
<212> TYPE: DNA
<213> ORGANISM: Artificial sequence
<220> FEATURE:
<223> OTHER INFORMATION: synthesized oligonucleotide
<220> FEATURE:
<221> NAME/KEY: misc_feature
<222> LOCATION: (1)..(8)
<223> OTHER INFORMATION: ethyl amidite
<220> FEATURE:
<221> NAME/KEY: modified_base
<222> LOCATION: (9)..(15)
<223> OTHER INFORMATION: 3-N-cyanoethyl-dT
<220> FEATURE:
<221> NAME/KEY: misc_feature
<222> LOCATION: (9)..(15)
<223> OTHER INFORMATION: n is a, c, g, or t
<220> FEATURE:
<221> NAME/KEY: misc_feature
<222> LOCATION: (16)..(30)
<223> OTHER INFORMATION: ethyl amidite

<400> SEQUENCE: 13
nnnnnnnnnn nnnnnnnnnn nnnnnnnnnn                                        30

<210> SEQ ID NO 14
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(6)
<223> OTHER INFORMATION: ethyl amidite
<220> FEATURE:
<221> NAME/KEY: misc_feature
<222> LOCATION: (9)..(9)
<223> OTHER INFORMATION: 1,4-bis-ethyl-benzene
<220> FEATURE:
<221> NAME/KEY: misc_feature
<222> LOCATION: (11)..(30)
<223> OTHER INFORMATION: ethyl amidite

<400> SEQUENCE: 14
nnnnnnttnt nnnnnnnnnn nnnnnnnnnn                                        30

<210> SEQ ID NO 15
<211> LENGTH: 30
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(9)
<223> OTHER INFORMATION: ethyl amidite
<220> FEATURE:
<221> NAME/KEY: misc_feature
<222> LOCATION: (11)..(12)
<223> OTHER INFORMATION: 1,4-bis-ethyl-benzene
<220> FEATURE:
<221> NAME/KEY: misc_feature
<222> LOCATION: (14)..(30)
<223> OTHER INFORMATION: ethyl amidite

<400> SEQUENCE: 15
nnnnnnnnnt nntnnnnnnn nnnnnnnnnn                                                30

<210> SEQ ID NO 16
<211> LENGTH: 28
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(8)
<223> OTHER INFORMATION: ethyl amidite
<220> FEATURE:
<221> NAME/KEY: misc_feature
<222> LOCATION: (9)..(11)
<223> OTHER INFORMATION: 1,4-bis-butyn-benzene
<220> FEATURE:
<221> NAME/KEY: misc_feature
<222> LOCATION: (12)..(28)
<223> OTHER INFORMATION: ethyl amidite

<400> SEQUENCE: 16 nnnnnnnnn nnnnnnnnn nnnnnnn                                                     28

<210> SEQ ID NO 17
<211> LENGTH: 31
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(8)
<223> OTHER INFORMATION: ethyl amidite
<220> FEATURE:
<221> NAME/KEY: misc_feature
<222> LOCATION: (15)..(30)
<223> OTHER INFORMATION: ethyl amidite
<220> FEATURE:
<221> NAME/KEY: misc_feature
<222> LOCATION: (31)..(31)
<223> OTHER INFORMATION: 3' propanol

<400> SEQUENCE: 17
nnnnnnnntt ttttnnnnnn nnnnnnnnnn n                                              31

<210> SEQ ID NO 18
<211> LENGTH: 31
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(8)
<223> OTHER INFORMATION: ethyl amidite
<220> FEATURE:

```
<221> NAME/KEY: modified_base
<222> LOCATION: (9)..(15)
<223> OTHER INFORMATION: 3-N-cyanoethyl-dT
<220> FEATURE:
<221> NAME/KEY: misc_feature
<222> LOCATION: (9)..(15)
<223> OTHER INFORMATION: n is a, c, g, or t
<220> FEATURE:
<221> NAME/KEY: misc_feature
<222> LOCATION: (16)..(30)
<223> OTHER INFORMATION: ethyl amidite
<220> FEATURE:
<221> NAME/KEY: misc_feature
<222> LOCATION: (31)..(31)
<223> OTHER INFORMATION: 3'-propanol

<400> SEQUENCE: 18 nnnnnnnnn nnnnnnnnn nnnnnnnnn n                                    31

<210> SEQ ID NO 19
<211> LENGTH: 31
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(6)
<223> OTHER INFORMATION: ethyl amidite
<220> FEATURE:
<221> NAME/KEY: misc_feature
<222> LOCATION: (9)..(9)
<223> OTHER INFORMATION: 1,4-bis-ethyl-benzene
<220> FEATURE:
<221> NAME/KEY: misc_feature
<222> LOCATION: (11)..(30)
<223> OTHER INFORMATION: ethyl amidite
<220> FEATURE:
<221> NAME/KEY: misc_feature
<222> LOCATION: (31)..(31)
<223> OTHER INFORMATION: 3'-propanol

<400> SEQUENCE: 19
nnnnnnttnt nnnnnnnnn nnnnnnnnn n                                    31

<210> SEQ ID NO 20
<211> LENGTH: 31
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(9)
<223> OTHER INFORMATION: ethyl amidite
<220> FEATURE:
<221> NAME/KEY: misc_feature
<222> LOCATION: (11)..(12)
<223> OTHER INFORMATION: 1,4-bis-ethyl-benzene
<220> FEATURE:
<221> NAME/KEY: misc_feature
<222> LOCATION: (14)..(30)
<223> OTHER INFORMATION: ethyl amidite
<220> FEATURE:
<221> NAME/KEY: misc_feature
<222> LOCATION: (31)..(31)
<223> OTHER INFORMATION: 3'-propanol

<400> SEQUENCE: 20
nnnnnnnnnt nntnnnnnnn nnnnnnnnn n                                    31

<210> SEQ ID NO 21
<211> LENGTH: 29
```

```
<212> TYPE: DNA
<213> ORGANISM: Artificial Sequence
<220> FEATURE:
<223> OTHER INFORMATION: synthesized oligonucleotide
<220> FEATURE:
<221> NAME/KEY: misc_feature
<222> LOCATION: (1)..(8)
<223> OTHER INFORMATION: ethyl amidite
<220> FEATURE:
<221> NAME/KEY: misc_feature
<222> LOCATION: (9)..(11)
<223> OTHER INFORMATION: 1,4-bis-butyn-benzene
<220> FEATURE:
<221> NAME/KEY: misc_feature
<222> LOCATION: (12)..(28)
<223> OTHER INFORMATION: ethyl amidite
<220> FEATURE:
<221> NAME/KEY: misc_feature
<222> LOCATION: (29)..(29)
<223> OTHER INFORMATION: 3'-propanol

<400> SEQUENCE: 21
nnnnnnnnnn nnnnnnnnnn nnnnnnnnn                               29

<210> SEQ ID NO 22
<211> LENGTH: 305
<212> TYPE: PRT
<213> ORGANISM: Staphylococcus aureus

<400> SEQUENCE: 22
```

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Thr Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr

-continued

|     | 245 |     |     | 250 |     |     |     | 255 |     |     |     |
|-----|-----|-----|-----|-----|-----|-----|-----|-----|-----|-----|-----|
| Gln Leu His Trp Thr Ser Thr Asn Trp Lys Gly Thr Asn Thr Lys Asp |
|     |     | 260 |     |     |     | 265 |     |     |     | 270 |     |
| Lys Trp Thr Asp Arg Ser Ser Glu Arg Tyr Lys Ile Asp Trp Glu Lys |
|     |     | 275 |     |     |     | 280 |     |     |     | 285 |     |
| Glu Glu Met Thr Asn Gly Leu Ser Ala Trp Ser His Pro Gln Phe Glu |
|     |     | 290 |     |     |     | 295 |     |     |     | 300 |     |
| Lys |
| 305 |

TAGGED NUCLEOTIDES USEFUL FOR NANOPORE DETECTION

FIELD

This application relates to compounds comprising a negatively-charged polymer moiety which is capable of entering a nanopore and upon entering a nanopore in the presence of positive ions results in an increased flow of the positive ions through the nanopore. The present disclosure provides methods of preparing the compounds and for their use as nanopore-detectable tags, in particular, for nanopore-based nucleic acid detection and sequencing.

REFERENCE TO SEQUENCE LISTING

The official copy of the Sequence Listing is submitted concurrently with the specification as an ASCII formatted text file with a file name of "04338-542WO1_SL_ST25.txt", a creation date of Aug. 11, 2017, and a size of 10,771 bytes. The Sequence Listing filed herewith is part of the specification and is incorporated in its entirety by reference herein.

BACKGROUND

Numerous methods for using nanopores to detect nucleic acids (e.g., DNA) or other molecules are known in the art. One common method involves applying an electric field across the nanopore to induce the nucleic acid to enter and partially block the nanopore, and measuring the current level and duration of the current blockage as the molecule rapidly enters and translocates through the pore. Both the current level and the duration of the blockage can reveal information about the molecule (typically, a polymeric molecule such as DNA). This type of nanopore detection method has also been carried out using polymeric polyethylene glycol (PEG) molecules and the length was of the polymer was found to affect both the current level and dwell time. See e.g., Joseph W. F. Robertson, Claudio G. Rodrigues, Vincent M. Stanford, Kenneth A. Rubinson, Oleg V. Krasilnikov, and John J. Kasianowicz, *Proc. Nat'l. Acad. Sci. USA,* 104; 8207 (2007).

Another method of observing a molecule using a nanopore is to attach a bulky moiety to the molecule so that it cannot pass, or cannot quickly pass, through the pore. An example is the use of the relatively bulky protein streptavidin that tightly binds biotin and Biotin can easily be covalently attached to DNA. With the DNA held between the pull of the electric field and the bulky protein, it can remain in a fixed position in the nanopore long enough to make an accurate measurement of pore current (milliseconds to seconds). It can then be released (e.g. by turning off or reversing the electric field) and the pore used again for another measurement. In addition to streptavidin, other proteins and molecules can be used as translocation blockers. For instance, antibodies which bind specific ligands or enzymes like DNA polymerase can be used. Even double-stranded DNA may be too large to pass through α-hemolysin pores, and it too can be used to hold DNA (or other polymers) in a fixed position in a nanopore under the pull of an electric field.

Nucleic acid sequencing is the process for determining the nucleotide sequence of a nucleic acid. Such sequence information may be helpful in diagnosing and/or treating a subject. For example, the sequence of a nucleic acid of a subject may be used to identify, diagnose, and potentially develop treatments for genetic diseases. As another example, research into pathogens may lead to treatment for contagious diseases. Since some diseases are characterized by as little as one nucleotide difference in a chain of millions of nucleotides, highly accurate sequencing is essential.

Single-molecule sequencing-by-synthesis (SBS) techniques using nanopores have been developed. See e.g., US Pat. Publ. Nos. 2013/0244340 A1, 2013/0264207 A1, 2014/0134616 A1. Nanopore SBS involves using a DNA polymerase (or other strand-extending enzyme) to synthesize a DNA strand complementary to a target sequence template and concurrently determining the identity of each nucleotide monomer as it is added to the growing strand, thereby determining the target sequence. Each added nucleotide monomer is detected by monitoring signals due to ion flow through a nanopore located adjacent to the polymerase active site over time as the strand is synthesized. Obtaining an accurate signal requires proper positioning of the polymerase active site near a nanopore, and the use of a tag on each added nucleotide which can enter the nanopore and provide an identifiable change in the ion flow through the pore. It also requires controlling the parameters of DNA polymerase strand extension reaction, including nucleotide monomer on-rate, processivity, transition rate, and overall read length. In order to provide for accurate nanopore sequencing, it is important for the tag to enter and reside in the nanopore for a sufficient amount of time (i.e., "dwell time"), and while residing in the nanopore, provide for a sufficiently detectable, and identifiable signal associated with the ion flow through the nanopore, such that the specific nucleotide associated with the tag can be distinguished unambiguously from the other tagged nucleotides.

Kumar et al., (2012) "PEG-Labeled Nucleotides and Nanopore Detection for Single Molecule DNA Sequencing by Synthesis," Scientific Reports, 2:684; DOI: 10.1038/srep00684, describes using a nanopore to distinguish four different length PEG-coumarin tags attached via a terminal 5'-phosphoramidate to a dG nucleotide, and separately demonstrates efficient and accurate incorporation of these four PEG-coumarin tagged dG nucleotides by DNA polymerase. See also, US Patent Application Publications US 2013/0244340 A1, published Sep. 19, 2013, US 2013/0264207 A1, published Oct. 10, 2013, and US 2014/0134616 A1, published May 14, 2014.

WO 2013/154999 and WO 2013/191793 describe the use of tagged nucleotides for nanopore SBS, and disclose the possible use of a single nucleotide attached to a single tag comprising branched PEG chains.

WO 2015/148402 describes the use of tagged nucleotides for nanopore SBS comprising a single nucleotide attached to a single tag, wherein the tag comprises any or a range of oligonucleotides (or oligonucleotide analogues) that have lengths of 30 monomer units or longer.

The above-described prior disclosures teach tagged nucleotide structures having a single nucleotide moiety attached to a single tag, or a branched tag. The general approach of these disclosures is to increase the size and structural variability of the tag and thereby facilitate better nanopore detection for SBS. The increased size these prior disclosed tagged nucleotides however creates a further obstacle to their utility for SBS by decreasing the substrate concentrations that can be achieved.

The above-described prior disclosures fail to teach specific tagged nucleotide structures that can provide high enough substrate concentrations to drive the polymerase extension reaction at rates desirable for efficient SBS, particularly in a nanopore setting where solution volumes are minimal and molecular concentrations critical. Accordingly, there remains a need for tagged nucleotide compositions and methods that can be used to improve efficiency and throughput in nanopore SBS and other sequencing techniques.

SUMMARY

The present disclosure provides compounds comprising a negatively-charged polymer moiety capable of entering a nanopore and upon entering the nanopore in the presence of positive ions results in an increased flow of the positive ions through the nanopore. Because of their ability to increase the flow of positive ions through a nanopore the compounds can be used as nanopore-detectable tags. Moreover, the ability of the compounds to increase the flow of positive ions provides for nanopore detectable signals that are above the "open channel" ("O.C.") current signal of a nanopore with no tag present, or the "blocking" or "blockade" signals that are below the O.C. current signal, and which is typical of known nanopore-detectable tags. This ability of the ion amplifying compounds of the present disclosure to provide nanopore-detectable signals above O.C. current allows for improved sensitivity and dynamic range for detection, and thereby increased accuracy in nanopore detection and sequencing applications.

Accordingly, the present disclosure also provides tagged nucleotide compounds comprising a nucleoside-5'-oligophosphate moiety capable of being a substrate for a polymerase and a tag, wherein the tag comprises a negatively-charged polymer moiety capable of entering a nanopore and upon entering the nanopore in the presence of positive ions results in an increased flow of the positive ions through the nanopore. The ion flow amplifying tagged nucleotide compounds of the present disclosure are well-suited for use in any nucleic acid sequencing-by-synthesis system that utilizes tagged nucleotides as polymerase substrates and identifies the unknown sequence by nanopore detection of the tagged by-products of the polymerase extension reaction. Additionally, the present disclosure also provides processes for preparing and using such ion flow amplifying compounds, the tagged nucleotide compounds, and methods for using these compounds in nanopore detection and nanopore sequencing of nucleic acids.

In some embodiments, the present disclosure provides a compound comprising a negatively-charged polymer moiety which is capable of entering a nanopore and upon entering a nanopore in the presence of positive ions results in an increased flow of the positive ions through the nanopore. In some embodiments, the compound further comprises a nucleoside-5'-oligophosphate moiety capable of being a substrate for a polymerase covalently linked to the polymer moiety.

In some embodiments, the disclosure provides a compound of structural formula (I)

(I)

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; and T is a tag covalently attached to the linker, wherein the tag comprises a negatively-charged polymer moiety which is capable of entering a nanopore and upon entering a nanopore in the presence of positive ions results in an increased flow of the positive ions through the nanopore.

In some embodiments, the compound of formula (I) has a structural formula (II)

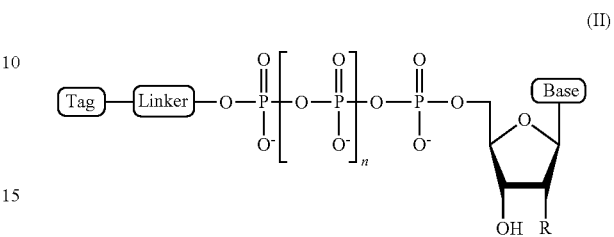

wherein, Base is selected from adenosine, cytidine, guanosine, thymidine, and uridine; R is selected from H and OH; n is from 1 to 4; Linker is a linker comprising a covalently bonded chain of 2 to 100 atoms; and Tag is a negatively-charged polymer moiety which is capable of entering a nanopore and upon entering a nanopore in the presence of positive ions results in an increased flow of the positive ions through the nanopore. In some embodiments, of the compounds of formula (I) or (II), the linker comprises a chemical group selected from the group consisting of: ester, ether, thioether, amine, amide, imide, carbonate, carbamate, squarate, thiazole, thiazolidine, hydrazone, oxime, triazole, dihydropyridazine, phosphodiester, polyethylene glycol (PEG), and any combination thereof.

In some embodiments, the compound of formula (II) has a structural formula (III)

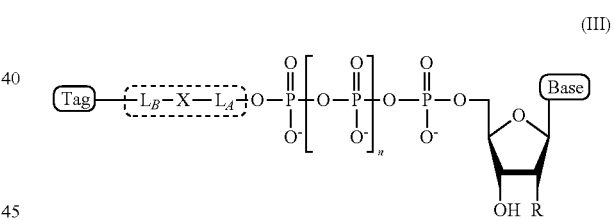

wherein, Base is selected from adenosine, cytidine, guanosine, thymidine, and uridine; R is selected from H and OH; n is from 1 to 4; $L_B$-X-$L_A$ is the linker, wherein (a) $L_A$ and $L_B$ each independently comprises a chemical moiety selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof; and (b) X comprises a chemical moiety selected from the group consisting of ester, ether, thioether, amine, amide, imide, carbonate, carbamate, squarate, thiazole, thiazolidine, hydrazone, oxime, triazole, and dihydropyridazine; and Tag is a negatively-charged polymer moiety which is capable of entering a nanopore and upon entering a nanopore in the presence of positive ions results in an increased flow of the positive ions through the nanopore.

In some embodiments, the compound of structural formula (III) has a structural formula (IIIa)

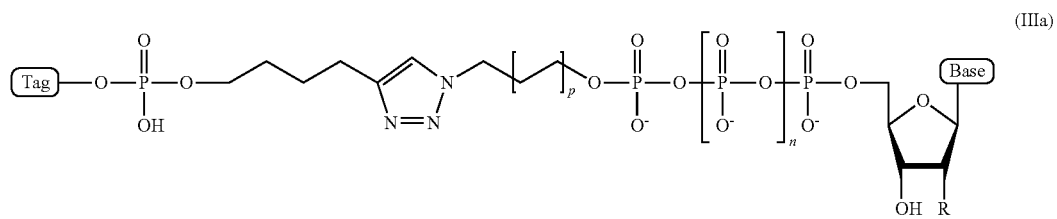

wherein, Base is selected from adenosine, cytidine, guanosine, thymidine, and uridine; R is selected from H and OH; n is from 1 to 4; p is from 2 to 10; and Tag is a negatively-charged polymer moiety which is capable of entering a nanopore and upon entering a nanopore in the presence of positive ions results in an increased flow of the positive ions through the nanopore. In some embodiment, the compound of structural formula (IIIa) is a compound wherein R=H, n=4, and p=5.

Generally, the ion-flow amplifying compounds of the present disclosure share the feature of a negatively-charged polymer moiety which is capable of entering a nanopore and upon entering a nanopore in the presence of positive ions results in an increased flow of the positive ions through the nanopore. The present disclosure provides a range of structural and functional parameters that characterize the negatively-charged polymer moiety of the compounds disclosed herein.

In some embodiments, the negatively-charged polymer moiety comprises a covalently linked chain of from 150 to 900 atoms with a negatively charged group attached to an atom of the chain at an interval of every 3 to 20 atoms, optionally an interval of every 3 to 10 atoms. In some embodiments, the covalently linked chain of from 150 to 900 atoms comprises chemical groups selected from phosphodiester, peptide, ester, ether, alkyl, alkenyl, alkynyl, perfluorinated alkyl, and any combination thereof. In some embodiments, the negatively-charged polymer moiety has a molecular length of between about 80 angstroms and about 250 angstroms and a molecular diameter of less than about 15 angstroms, optionally a molecular diameter of less than about 12 angstroms, or optionally a molecular diameter of less than about 10 angstroms. In some embodiments, the negatively-charged polymer moiety has at least one negative charge per 10 angstroms of molecular length, optionally at least one negative charge per 7.5 angstroms of molecular length, or at least one negative charge per 3.5 angstroms of molecular length. In some embodiments, the negatively-charged polymer moiety has an overall negative charge of from (−25) to (−50), optionally an overall negative charge of from (−30) to (−40), or optionally an overall negative charge of from (−31) to (−37).

In some embodiments, the negatively-charged polymer moiety comprises a covalently linked chain of from 20 to 50 monomer units, optionally from 25 to 40 monomer units, or optionally from 27 to 35 monomer units. In some embodiments, the monomer units comprise a negatively-charged group attached to a covalently linked chain of from 3 to 20 atoms, optionally a chain of from 3 to 10 atoms. In some embodiments, the monomer units comprise covalent links selected from the group consisting of phosphodiester, peptide, ester, ether, alkyl, alkenyl, alkynyl, perfluoroalkyl, and any combination thereof. In some embodiments, the monomer units comprise a negatively charged group selected from the group consisting of phosphate, sulfate, carboxylate, and any combination thereof. In some embodiments, the monomer units are selected from the group consisting of the structures of formula (1a), (1b), (1c), (1d), (1e), (1f), (1g), (1h), (1i), (1j), (1k), (1l), (1m), (2a), (2b), (2c), (3a), (3b), (3c), and any combination thereof

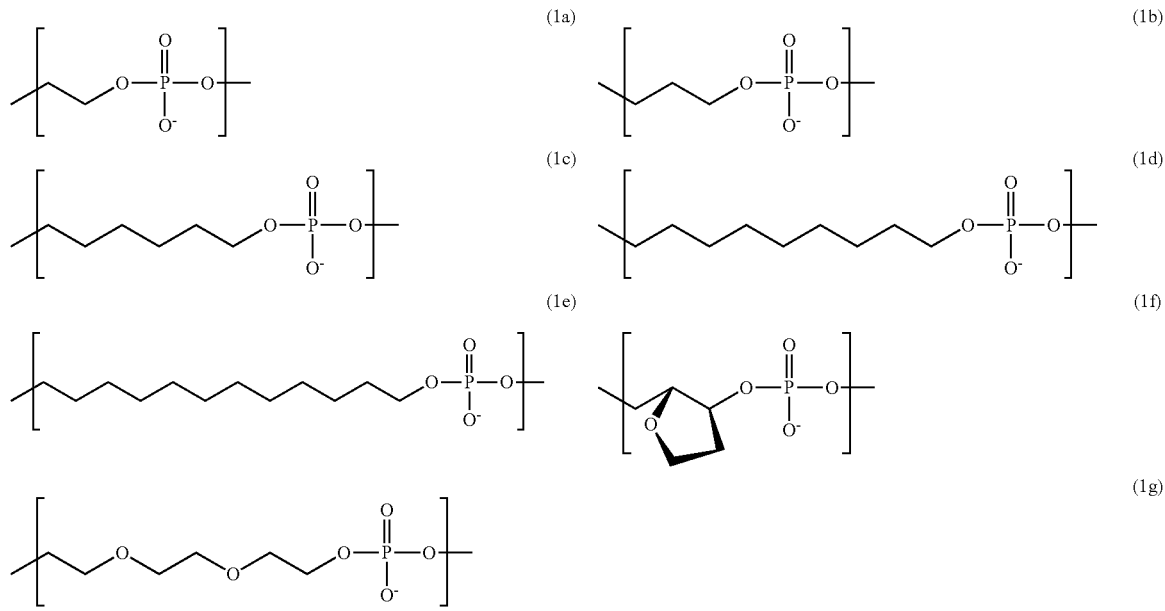

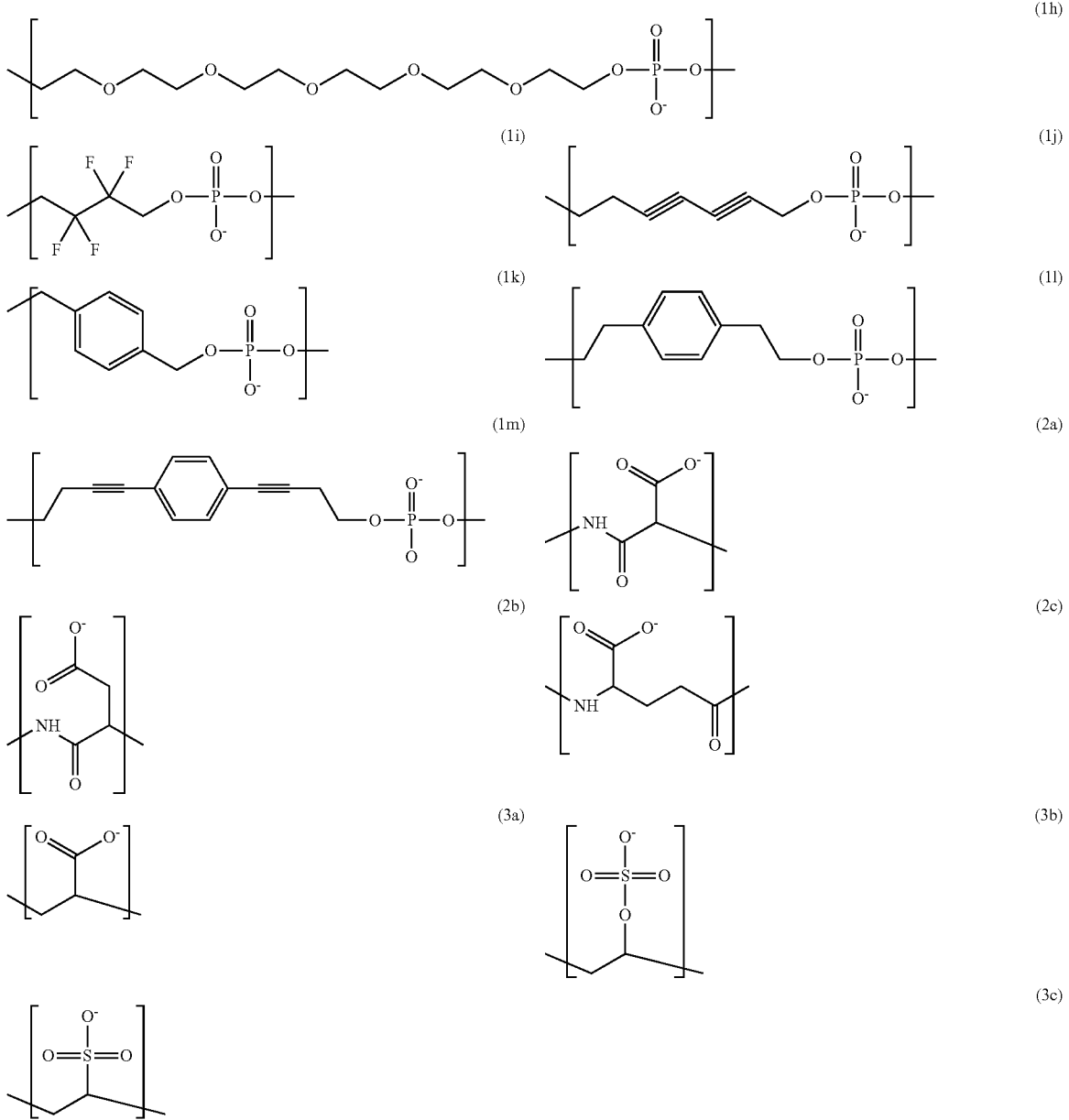

In some embodiments, the negatively-charged polymer moiety comprises an oligonucleotide of formula $(A)_n$, wherein A is a monomer unit independently selected from the monomer unit structures of formula (1a), (1b), (1c), (1d), (1e), (1f), (1g), (1h), (1i), (1j), (1k), (1l), and (1m), and n is from 10 to 40, optionally n is from 20 to 40, n is from 25 to 35, or n is from 27 to 35. In some embodiments, the negatively-charged polymer moiety comprises an oligonucleotide of formula $(A)_m$-$(B)_n$-$(C)_p$-$(D)_q$, wherein A, B, C, and D, are monomer units independently selected from the monomer unit structures of formula (1a), (1b), (1c), (1d), (1e), (1f), (1g), (1h), (1i), (1j), (1k), (1l), and (1m), and each of m, n, p, and q is from 0 to 40, and m+n+p+q is from 10 to 40, optionally m+n+p+q is from 20 to 40, m+n+p+q is from 25 to 35, or m+n+p+q is from 27 to 35.

In some embodiments, the negatively-charged polymer moiety comprises an oligonucleotide selected from the group consisting of: -TT-$(SpC2)_{28}$- (SEQ ID NO: 1), -TT-$(SpC3)_{28}$- (SEQ ID NO: 2), -$(SpC3)_{31}$- (SEQ ID NO: 3), -TT-$(dSp)_{26}$-TT- (SEQ ID NO: 4), -TT-$(SpC4\text{-}F4)_{28}$- (SEQ ID NO: 5), -TT-$(SpC7\text{-}Pra2)_{28}$- (SEQ ID NO: 6), -$(SpC2)_8$-$T_6$-$(SpC2)_{16}$-(SEQ ID NO: 12), -$(SpC2)_8$-$(N3CEdT)_7$-$(SpC2)_{15}$- (SEQ ID NO: 13), -$(SpC2)_6$-TT-(BHEB)-T-$(SpC2)_{20}$- (SEQ ID NO: 14, -$(SpC2)_9$-T-$(BHEB)_2$-T-$(SpC2)_{17}$- (SEQ ID NO: 15), and -$(SpC2)_8$-$(S500)_3$-$(SpC2)_{17}$- (SEQ ID NO: 16).

In some embodiments, the increased ion flow induced by the negatively-charged polymer moiety results in a measured current across the nanopore that is greater than O.C. current, optionally at least 5% greater than O.C. current, at least 10% greater than O.C. current, at least 25% greater than O.C. current, or at least 50% greater than O.C. current.

In some embodiments, the present disclosure also provides compositions comprising at least one of the ion-flow amplifying compounds. In some embodiments, the composition comprises a set of compounds, wherein each compound of the set comprises a different tag which results in a different flow of positive ions through a nanopore when the tag enters the nanopore, and at least one of the compounds of the set is a compound comprising a negatively-charged polymer moiety (as provided herein) which is capable of entering a nanopore and upon entering a nanopore in the presence of positive ions results in an increased flow of the positive ions through the nanopore, and thereby resulting in a measured current across the nanopore that is greater than O.C. current. In one embodiment of the composition, the set of compounds comprises the tagged nucleotide compounds dA6P-(Linker)-$T_{30}$-C3; dC6P-(Linker)-TT-$(dSp)_{26}$-TT-C3; dG6P-(Linker)-TT-$(SpC2)_{28}$-biotin; dT6P-(Linker)-TT-$(SpC3)_{28}$-biotin; wherein, "(Linker)" refers to a linker of formula (XVd)

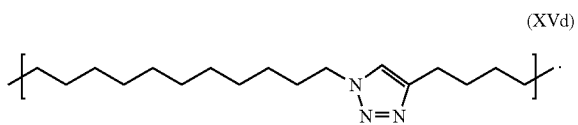

(XVd)

The present disclosure also provides methods of using the ion-flow amplifying compounds. Accordingly, in some embodiments, the disclosure provides method for determining the sequence of a nucleic acid comprising: (a) providing a nanopore sequencing composition comprising: a membrane, an electrode on the cis side and the trans side of the membrane, a nanopore with its pore extending through the membrane, an electrolyte solution comprising positive ions in contact with both electrodes, an active polymerase situated adjacent to the nanopore, and a primer strand complexed with the polymerase; (b) contacting the nanopore sequencing composition with (i) a strand of the nucleic acid; and (ii) a set of compounds each comprising a different nucleoside-5'-oligophosphate moiety covalently linked to a tag, wherein each member of the set of compounds has a different tag which results in a different flow of positive ions through a nanopore when the tag enters the nanopore, and at least one of the different tags comprises a negatively-charged polymer moiety which upon entering a nanopore in the presence of positive ions results in an increased flow of the positive ions through the nanopore; and (c) detecting the different flows of positive ions resulting from the entry of the different tags in the nanopore over time and correlating to each of the different compounds incorporated by the polymerase which are complementary to the nucleic acid sequence, and thereby determining the nucleic acid sequence.

BRIEF DESCRIPTION OF THE DRAWINGS

FIG. 1 depicts a plot of a series of ion flow amplifying tag signals (above open channel current) detected over time in a sequencing by synthesis experiment using a nanopore array device comprising Pol6 polymerase conjugated to an α-hemolysin nanopore as described in Example 2.

DETAILED DESCRIPTION

For the descriptions herein and the appended claims, the singular forms "a", and "an" include plural referents unless the context clearly indicates otherwise. Thus, for example, reference to "a protein" includes more than one protein, and reference to "a compound" refers to more than one compound. The use of "comprise," "comprises," "comprising" "include," "includes," and "including" are interchangeable and not intended to be limiting. It is to be further understood that where descriptions of various embodiments use the term "comprising," those skilled in the art would understand that in some specific instances, an embodiment can be alternatively described using language "consisting essentially of" or "consisting of."

Where a range of values is provided, unless the context clearly dictates otherwise, it is understood that each intervening integer of the value, and each tenth of each intervening integer of the value, unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding (i) either or (ii) both of those included limits are also included in the invention. For example "1 to 50" includes "2 to 25", "5 to 20", "25 to 50", "1 to 10", etc.

It is to be understood that both the foregoing general description, including the drawings, and the following detailed description are exemplary and explanatory only and are not restrictive of this disclosure.

Definitions

"Nucleic acid," as used herein, refers to a molecule of one or more nucleic acid subunits which comprise one of the nucleobases, adenine (A), cytosine (C), guanine (G), thymine (T), and uracil (U), or variants thereof. Nucleic acid can refer to a polymer of nucleotides (e.g., dAMP, dCMP, dGMP, dTMP), also referred to as a polynucleotide or oligonucleotide, and includes DNA, RNA, in both single and double-stranded form, and hybrids thereof.

"Nucleotide," as used herein refers to a nucleoside-5'-oligophosphate compound, or structural analog of a nucleoside-5'-oligophosphate, which is capable of acting as a substrate or inhibitor of a nucleic acid polymerase. Exemplary nucleotides include, but are not limited to, nucleoside-5'-triphosphates (e.g., dATP, dCTP, dGTP, dTTP, and dUTP); nucleosides (e.g., dA, dC, dG, dT, and dU) with 5'-oligophosphate chains of 4 or more phosphates in length (e.g., 5'-tetraphosphate, 5'-pentaphosphate, 5'-hexaphosphate, 5'-heptaphosphate, 5'-octaphosphate); and structural analogs of nucleoside-5'-triphosphates that can have a modified base moiety (e.g., a substituted purine or pyrimidine base), a modified sugar moiety (e.g., an O-alkylated sugar), and/or a modified oligophosphate moiety (e.g., an oligophosphate comprising a thiophosphate, a methylene, and/or other bridges between phosphates).

"Nucleoside," as used herein, refers to a molecular moiety that comprises a naturally occurring or non-naturally occurring nucleobase attached to a sugar moiety (e.g., ribose or deoxyribose).

"Oligophosphate," as used herein, refers to a molecular moiety that comprises an oligomer of phosphate groups. For example, an oligophosphate can comprise an oligomer of from 2 to 20 phosphates, an oligomer of from 3 to 12 phosphates, an oligomer of from 3 to 9 phosphates.

"Polymerase," as used herein, refers to any natural or non-naturally occurring enzyme or other catalyst that is capable of catalyzing a polymerization reaction, such as the polymerization of nucleotide monomers to form a nucleic acid polymer. Exemplary polymerases that may be used in the compositions and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1).

"Moiety," as used herein, refers to part of a molecule.

"Linker," as used herein, refers to any molecular moiety that provides a bonding attachment with some space between two or more molecules, molecular groups, and/or molecular moieties.

"Tag," as used herein, refers to a moiety or part of a molecule that enables or enhances the ability to detect and/or identify, either directly or indirectly, a molecule or molecular complex, which is coupled to the tag. For example, the tag can provide a detectable property or characteristic, such as steric bulk or volume, electrostatic charge, electrochemical potential, optical and/or spectroscopic signature.

"Nanopore," as used herein, refers to a pore, channel, or passage formed or otherwise provided in a membrane or other barrier material that has a characteristic width or diameter of about 1 angstrom to about 10,000 angstroms. A nanopore can be made of a naturally-occurring pore-forming protein, such as α-hemolysin from S. aureus, or a mutant or variant of a wild-type pore-forming protein, either non-naturally occurring (i.e., engineered) such as α-HL-C46, or naturally occurring. A membrane may be an organic membrane, such as a lipid bilayer, or a synthetic membrane made of a non-naturally occurring polymeric material. The nanopore may be disposed adjacent or in proximity to a sensor, a sensing circuit, or an electrode coupled to a sensing circuit, such as, for example, a complementary metal-oxide semiconductor (CMOS) or field effect transistor (FET) circuit.

"Nanopore-detectable tag" as used herein refers to a tag that can enter into, become positioned in, be captured by, translocate through, and/or traverse a nanopore and thereby result in a detectable change in current through the nanopore. Exemplary nanopore-detectable tags include, but are not limited to, natural or synthetic polymers, such as polyethylene glycol, oligonucleotides, polypeptides, carbohydrates, peptide nucleic acid polymers, locked nucleic acid polymers, any of which may be optionally modified with or linked to chemical groups, such as dye moieties, or fluorophores, that can result in detectable nanopore current changes.

"Ion flow," as used herein, refers to the movement of ions, typically in a solution, due to an electromotive force, such as the potential between an anode and a cathode. Ion flow typically can be measured as current or the decay of an electrostatic potential.

"Ion flow amplifying," or "ion flow enhancing," as used herein in the context of nanopore detection, refers to the characteristic of resulting in an increase in ion flow through a nanopore greater than the ion flow through the nanopore in its "open channel" (O.C.) state.

"Open channel current," "O.C. current," or "Background current" as used herein refers to the current level measured across a nanopore when a potential is applied and the nanopore is open (e.g., no tag is present in the nanopore).

"Tag current" as used herein refers to the current level measured across a nanopore when a potential is applied and a tag is present the nanopore. Typically, the presence of a tag in a nanopore results in a blocking of ion flow through the nanopore and a result decrease in measure tag current level. The ion flow amplifying tags of the present disclosure, however, when present in a nanopore result in an increased ion flow indicated in a tag current level measured across a nanopore greater than O.C. current.

"Dwell time" as used herein in the context of capture of a tag in a nanopore refers to the time that the tag spends in the nanopore as detected by a tag current.

"Molecular length," as used herein, refers to the average length of a molecule (or a moiety) at its longest axial dimension when the molecule (or moiety) is in its average solution conformation.

"Molecular diameter," as used herein, refers to the average length of a molecule (or a moiety) at its the shortest axial dimension when the molecule (or moiety) is in its average solution conformation.

"Overall charge," as used herein, refers to the sum of the positively and negatively charged chemical groups that make up a molecule (or a moiety). For example, a tag moiety comprising a polymer of 30 monomer units with 30 phosphodiester groups (each of which has a charge of (−1) at pH 7) is a negatively-charged polymer with an overall charge of (−30).

"Negatively-charged," as used herein in the context of a tag moiety refers to a tag moiety having an overall charge that is negative.

DETAILED DESCRIPTION OF VARIOUS EMBODIMENTS

Overview: Ion-Flow Amplifying Tags and Nanopore Sequencing

The present disclosure describes compositions of ion flow amplifying tagged nucleotide compounds and related methods, devices, and systems that are useful for nanopore detection and sequencing of nucleic acids. The ion flow amplifying tagged nucleotide compounds can be used in methods to accurately detect individual nucleotide incorporation by a nucleic acid polymerase into a growing strand that is complementary to a template nucleic acid strand.

Generally, nanopore-based nucleotide acid sequencing uses a mixture of four nucleotide analogs (e.g., dA6P, dC6P, dG6P, and dT6P) that can be incorporated by an enzyme into a growing strand. Each nucleotide analog has a covalently attached tag moiety that provides an identifiable, and distinguishable signature when detected with a nanopore. The strand extending enzyme (e.g., DNA polymerase) specifically binds the tagged nucleotide compound that is complimentary to a template nucleic acid strand which is hybridized to the growing nucleic acid strand at its active site. The strand extending enzyme then catalytically couples (i.e., incorporates) the complimentary nucleotide moiety of the tagged nucleotide compound to the end of the growing nucleic acid strand. Completion of the catalytic incorporation event results in the release of the tag moiety and the oligophosphate moiety (minus the one phosphate incorporated into the growing strand) which then passes through the adjacent nanopore. Even before it undergoes catalytic process that releases it from the incorporated nucleotide however, the tag moiety of a tagged nucleotide compound enters the pore of the nanopore under an applied potential and thereby alters the background positive ion flow through the nanopore. Generally, the presence of a tag moiety in a nanopore results in decreasing (or blocking) the flow of positive ions through the nanopore. This "blocking current" is detected as signal that is a percentage of (or below) the "open channel" (or "O.C.") current resulting from positive ion flow through the nanopore with no tag moiety present.

To date, various molecular properties of tag moieties have been modified (e.g., mass, volume, 3-D structure, electrostatic charge) and found to affect the interaction with the pore, thereby allowing for nanopore detection to distinguish different tag moieties each of which can correspond to a different nucleotide. A variety of nanopore systems and methods for using them to detect tagged molecules including tagged nucleotides for nucleic acid sequencing are known in the art. See, for example, U.S. patent application Ser. No. 12/308,091, Ju et al., filed May 18, 2009; U.S. patent application Ser. No. 13/994,431, Ju et al., filed Jun. 14, 2013; US Patent Application Publications US 2013/0244340 A1, published Sep. 19, 2013, US 2013/0264207 A1, published Oct. 10, 2013, and US 2014/0134616 A1, published May 14, 2014; PCT Appl. No. PCT/US13/35635, Ju et al., filed Apr. 8, 2013; and PCT Appl. No. PCT/US13/35640, Ju et al., filed Apr. 8, 2013, PCT International Publication No. WO2015/148402, US Provisional Patent Appl. Nos. 62/235,551, filed Sep. 30, 2015, and 62/216,634, filed Sep. 10, 2015, each of which is hereby incorporated herein by reference in its entirety.

All prior known tag moieties used for nanopore detection, however, result in a "blocking" current signal resulting from a decrease in positive ion flow through the nanopore. The surprising result provided by the present disclosure is that certain tag moiety structures comprising negatively-charged polymers are capable of entering a nanopore and upon entering the nanopore in the presence of positive ions result in an increased flow of the positive ions through the nanopore. These ion flow amplifying tag moiety structures provide a whole new range nanopore detectable signals that occur above the open channel current and below "blocking" signal range for detection known in the art.

Tagged Nucleotide Compound Structures

The present disclosure provides ion flow amplifying compounds useful as tags, and ion flow amplifying tagged compound embodiments (e.g., tagged nucleotides) that can be characterized by a range of structures and sub-structures. Generally, the ion flow amplifying tagged compound of the present disclosure comprises a negatively-charged polymer moiety which is capable of entering a nanopore and upon entering a nanopore in the presence of positive ions results in an increased flow of the positive ions through the nanopore.

Generally, the ion flow amplifying tagged nucleotide compound of the present disclosure comprises an ion flow amplifying tag moiety covalently linked to a nucleoside-5'-oligophosphate moiety, wherein the tag moiety comprises a negatively-charged polymer moiety which is capable of entering a nanopore and upon entering a nanopore in the presence of positive ions results in an increased flow of the positive ions through the nanopore. In some embodiments, the ion flow amplifying tagged nucleotide comprises an ion flow amplifying compound (e.g., ion flow amplifying tag) and further comprises a nucleoside-5'-oligophosphate moiety capable of being a substrate for a polymerase covalently linked to the polymer moiety As described elsewhere herein, the ion flow amplifying tag moieties of the present disclosure result in technical advantages including increased dynamic range and sensitivity for nanopore detection of the tagged compounds (e.g., tagged nucleotides) due to their ability to result in a measured current signal that is greater than the O.C. signal. In some embodiments, the increased ion flow results in an increased measured current across a nanopore that is at least 10%, 15%, 20%, 25%, 30%, 40%, 50%, 75%, 90%, or greater than the O.C. signal across the nanopore.

Although the present disclosure describes numerous embodiments where the ion flow amplifying tag moieties of the present disclosure can be used in tagged nucleotide compounds for nanopore based sequencing-by-synthesis (SBS) methods, it is also contemplated that the ion flow amplifying tag moieties can be conjugated to other types of compounds and used as tags in any method that involves nanopore detection of a tagged compound. It is contemplated that any of assay using nanopore detection of a tagged compound could be easily adapted to use an ion flow amplifying tag moiety. Thus, the ordinary artisan can use the synthesis methods disclosed herein to prepare ion flow amplifying tagged nucleotide compounds to prepare other tagged compound using the ion amplifying tag moiety structures disclosed herein.

In some embodiments, the present disclosure provides an ion flow amplifying tagged nucleotide compound of structural formula (I)

$$N\text{-}P\text{-}L\text{-}T \qquad (I)$$

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; and T is a tag covalently attached to the linker, wherein the tag comprises a negatively-charged polymer moiety which is capable of entering a nanopore and upon entering a nanopore in the presence of positive ions results in an increased flow of the positive ions through the nanopore.

The nucleoside (N) can be any nucleoside capable of being incorporated by a strand-extending enzyme, such as a polymerase, when the nucleoside is covalently coupled to an oligophosphate (P), such as a triphosphate. The nucleoside can comprise a naturally occurring or non-naturally occurring nucleobase, and a naturally occurring or non-naturally occurring sugar moiety, such as a ribose or deoxyribose group. In some embodiments, the nucleobase is selected from group consisting of adenosine, cytidine, guanosine, thymidine, and uridine. The sugar moiety should provide a free hydroxyl group at a position (e.g., a 3'-OH group) that can form a phosphodiester bond with a growing polynucleotide strand when catalytically incorporated by a strand extending enzyme. The nucleoside sugar moiety should also provide a group allowing covalent attachment of an oligophosphate moiety (e.g., a 5'-O group).

In some embodiments, the present disclosure provides an ion flow amplifying tagged nucleotide compound of structural formula (II)

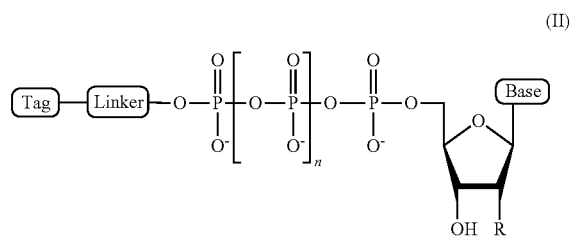

(II)

wherein, Base is selected from adenosine, cytidine, guanosine, thymidine, and uridine; R is selected from H and OH; n is from 1 to 4; Linker is a linker comprising a covalently bonded chain of 2 to 100 atoms; and Tag is a tag comprising a negatively-charged polymer moiety which is capable of entering a nanopore and upon entering a nanopore in the presence of positive ions results in an increased flow of the positive ions through the nanopore.

In some embodiments, the nucleobase ("Base") can be any naturally or non-naturally occurring (e.g., chemically modified) base which is capable of being incorporated by a strand-extending enzyme, such as a polymerase. In some embodiments, the nucleobase is selected from group consisting of adenosine, cytidine, guanosine, thymidine, and uridine.

The oligophosphate (P) moiety of the ion flow amplifying tagged nucleotide compounds can be any oligophosphate which, when attached to the 5'-O of the nucleoside, allows the resulting nucleotide to still be capable of being incorporated by a strand-extending enzyme, such as a polymerase. Generally, strand-extending enzymes, such as polymerase, are capable of incorporating nucleotides comprising oligophosphates having chains of from 3 to 12 phosphate groups. Accordingly, in an ion flow amplifying tagged nucleotide compound of the present disclosure (e.g., the compound of structural formula (I) or (II)) the oligophosphate (P) group can comprise 3 to 12 phosphate groups.

As depicted in the compound of structural formula (II), the oligophosphate of 3 to 12 phosphate groups would be represented by values of $n=1$ to $n=10$. Thus, in some embodiments of the present disclosure, the ion flow amplifying tagged nucleotide compound comprises an oligophosphate (P) group comprising 3 to 9 phosphate groups (or $n=1$ to 7 for formula (II)). In some embodiments, the oligophosphate group comprises 4 to 6 phosphate groups (or $n=2$ to 4 for formula (II)). In some embodiments, the oligophosphate group comprises 6 phosphate groups (or $n=4$ for formula (II)).

In other embodiments, the ion flow amplifying tagged nucleotide compounds of the present disclosure can comprise oligophosphate chains of 4 to 20 phosphates, 4 to 12 phosphates, 4 to 9 phosphates, 4 to 6 phosphates, wherein the chain is attached at the 5' position of the nucleoside (e.g., 5'-tetraphosphate, 5'-pentaphosphate, 5'-hexaphosphate, 5'-heptaphosphate, 5'-octaphosphate, 5'-nonaphosphate, 5'-decaphosphate, etc.).

It is further contemplated that the ion flow amplifying tagged nucleotide compounds of the present disclosure, can include oligophosphate moieties comprising modified phosphate groups, phosphate analogs, or other non-phosphate chemical groups, provided that the inclusion of such phosphate groups does not prevent the resulting ion flow amplifying tagged nucleotide from being incorporated by a strand-extending enzyme when the oligophosphate is attached to the 5'-O of the nucleoside. Typically, incorporation by a strand-extending enzyme requires a naturally occurring phosphate group at the α-position and a phosphodiester bond between the α-position and n-positions of the oligophosphate. Thus, in some embodiments, the oligophosphate can comprise a thiophosphate group. Additionally, it is contemplated that the oligophosphate can include an oligomer of phosphate or phosphate-analog groups with one or more non-phosphate groups, such as a methylene, and/or a bridging group between two or more phosphate groups.

Linkers

It is contemplated that a wide range of linkers can be used to covalently couple the ion flow amplifying tag moieties of the present disclosure to a compound desired to be tagged for nanopore detection (e.g., tagged nucleotide compound). Generally, the linker can comprise any molecular moiety that is capable of providing a covalent coupling and a spacing or structure between the compound and the tag moiety that is desired for the particular nanopore detection method. Such linker parameters can be routinely determined by the ordinary artisan using methods known in the art.

In some embodiments, the desired spacing or structure can be selected and optimized for the specific use of the ion flow amplifying tagged nucleotide compound. For example, a linker can be selected that provides a spacing that allows the ion flow amplifying tag moiety to enter and reside in the nanopore when any one of the multiple tagged nucleotides forms a ternary complex with an adjacent polymerase. Generally, the negatively charged polymer structure of the ion flow amplifying tag moiety should adopt a narrow and elongated rod-like conformation such that it capable of entering the nanopore having its length approximately spanning the length of the nanopore. Depending on how the polymerase is coupled to the nanopore, a linker of a slightly shorter or longer length may be selected so as to allow the ion flow amplifying tag moiety to attain this nanopore spanning position (and provide the optimal ion flow enhancement associate signal) when the tagged nucleotide forms a proper ternary complex at the polymerase active site.

Generally, the linkers useful with the ion flow amplifying tagged nucleotide compounds of the present disclosure (e.g., compounds of formulas (I) and (II)) comprise a covalently bonded chain of 2 to 100 atoms. In some embodiments, the linker chain of 2 to 100 atoms comprises one or more chemical moieties selected from the group consisting of: linear ($C_1$-$C_{12}$) alkyl, linear ($C_1$-$C_{12}$) alkene, linear (C1-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof. A variety of linkers comprising a range of chemical moieties that are useful in the ion flow amplifying tagged compounds of the present disclosure are described and exemplified herein.

Typically, in the ion flow amplifying tagged nucleotide embodiments of the present disclosure, the linker is formed during the preparation of a compound of structural formula (I) or (II), in a chemical reaction that covalent couples the terminal phosphate (or phosphate analog) of the oligophosphate moiety to the tag, or to a linker moiety that is attached to, or can be covalently attached to the tag. More specifically, this chemical reaction typically involves a tag moiety modified with a reactive linker-forming group and a nucleotide comprising an oligophosphate moiety, wherein the terminus of the oligophosphate is also modified with a reactive linker-forming group. This type of linker forming chemical reaction can be depicted in a tagged nucleotide compound of formula (III) as in Scheme 1.

Scheme 1

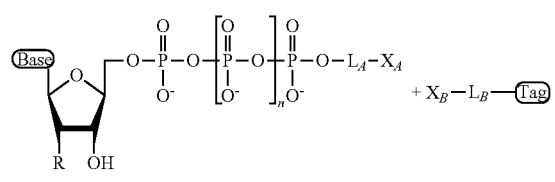

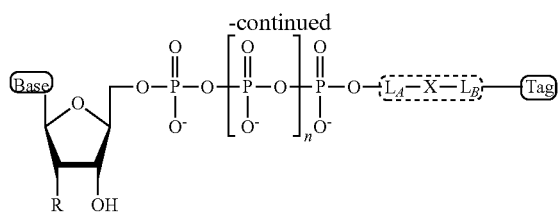

As depicted in Scheme 1, $X_A$ and $X_B$ are reactive linker forming groups, and $L_A$ and $L_B$, are precursor linker moieties to the finally formed linkers of structure -$L_B$-X-$L_A$- found in the tagged nucleotide compound of formula (III). Thus, $X_A$ and $X_B$ are chemical moieties which are capable of undergoing a chemical reaction that results in a covalent coupling between one of the multiple nucleotide and the tag. The product of each covalent coupling reaction between the linker forming groups, $X_A$ and $X_B$, is a linker comprising a general structure -$L_B$-X-$L_A$-. Thus, in some embodiments of the present disclosure, the linker "L" or "Linker" as in the compounds of formula (I) and (II) is a linker of structural formula "-$L_B$-X-$L_A$-" as depicted in Scheme 1.

The chemical moiety, "X" (of the "-$L_B$-X-$L_A$-") of structural formula (III) is the new chemical linker moiety produced in the linker forming reaction. Often, the name of the particular chemical group X is used to denote the type of linker, although the other parts of the linker provided by $L_A$ and $L_B$ may contribute substantially to the overall structure of the linker. In some embodiments, the linker comprises a chemical moiety, X, produced in the linker forming reaction between the linker forming reagents, $X_A$ and $X_B$, wherein X is a chemical moiety selected from the group consisting of ester, ether, thioether, amine, amide, imide, carbonate, carbamate, squarate, thiazole, thiazolidine, hydrazone, oxime, triazole, dihydropyridazine, phosphodiester, and polyethylene glycol (PEG).

The chemical moieties, $L_A$ and $L_B$ are chemical groups which can effectively act as linkers or spacers between the nucleoside-5'-oligophosphate moiety or the tag moiety and their linker forming reagent groups, $X_A$ and $X_B$. Typically, $L_A$ and $L_B$ are chemical moieties that do not react in the linker forming reaction but which provide additional spacing or structure for the final formed linker. The $L_A$ and $L_B$ moieties can be the same or different. In some embodiments, $L_A$ or $L_B$ can be much longer or shorter than the other, and/or provide different structural features, for example features that result in more or less conformational flexibility. Accordingly, in some embodiments, $L_A$ and $L_B$ moieties useful in the ion flow amplifying tagged nucleotide compounds of the present disclosure comprise a covalently bonded chain of 2 to 100 atoms, and optionally, one or more chemical moieties selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof.

Thus, in some embodiments, the present disclosure provides an ion flow amplifying tagged nucleotide compound of structural formula (III)

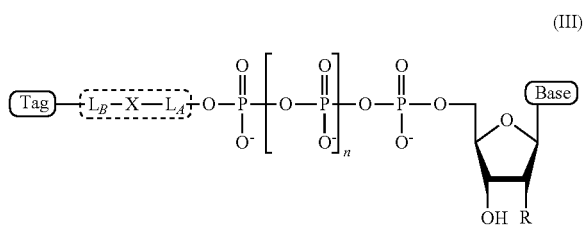

wherein, Base is selected from adenosine, cytidine, guanosine, thymidine, and uridine; R is selected from H and OH; n is from 1 to 4; $L_B$-X-$L_A$ is the linker, wherein (a) $L_A$ and $L_B$ each independently comprises a chemical moiety selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof; and (b) X comprises a chemical moiety selected from the group consisting of ester, ether, thioether, amine, amide, imide, carbonate, carbamate, squarate, thiazole, thiazolidine, hydrazone, oxime, triazole, and dihydropyridazine; In some embodiments, $L_A$ and $L_B$; and Tag is a tag comprising a negatively-charged polymer moiety which is capable of entering a nanopore and upon entering a nanopore in the presence of positive ions results in an increased flow of the positive ions through the nanopore.

In some embodiments, the characteristic linker moiety X is a triazole group. Such a triazole group can be formed in a "click" reaction between an azide linker forming reagent, and an alkyne linker forming reagent. In addition, it is contemplated that a linker in a compound of structural formula (III) comprising a triazole group X can further comprise include a linear alkyl and/or amide groups on one or both sides of the triazole group. Accordingly, in one embodiment, the present disclosure provides an ion flow amplifying tagged nucleotide compound of structural formula (IIIa)

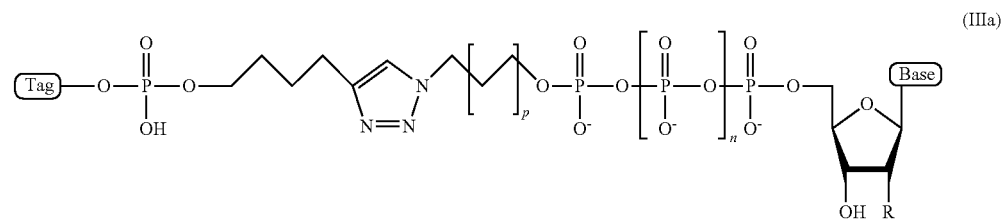

wherein, Base is selected from adenosine, cytidine, guanosine, thymidine, and uridine; R is selected from H and OH; n is from 1 to 4; p is from 2 to 10; and Tag is a tag comprising a negatively-charged polymer moiety which is capable of entering a nanopore and upon entering a nanopore in the presence of positive ions results in an increased flow of the positive ions through the nanopore. In some embodiments of the tagged nucleotide compound of structural formula (IIIa), the compound comprises the structural parameters R is H, n=4, and p=5, resulting in the compound of formula (IIId)

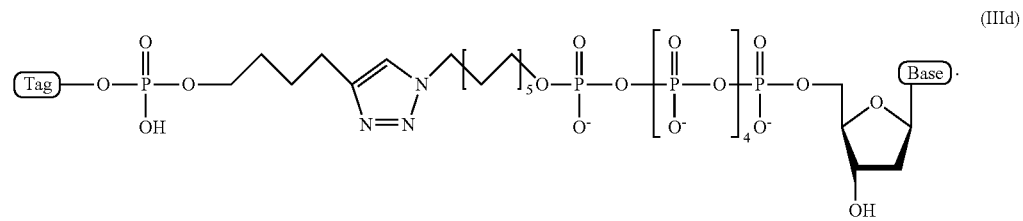

(IIId)

Exemplary linker forming groups, $X_A$ and $X_B$, linker precursor moieties, $L_A$ and $L_B$ and the resulting linker that they form, of formula $-L_A-X-L_B-$, are shown in Table 1, below.

TABLE 1

| $R_1-L_A-X_A*$ | $X_B-L_B-R_2*$ | $R_1-L_A-X-L_B-R_2*$ (or $R_1$-Linker-$R_2$) |
|---|---|---|
| (IVa) | (IVb) | (IVc) |
| (Va) | (Vb) | (Vc) |
| (VIa) | (VIb) | (VIc) |
| (VIIa) | (VIIb) wherein, Z is a suitable leaving group, e.g., F, Cl, Br, or I | (VIIc) |
| (VIIIa) | (VIIIb) | (VIIIc) |

TABLE 1-continued
| R₁—L_A—X_A* | X_B—L_B—R₂* | R₁—L_A—X—L_B—R₂* (or R₁-Linker-R₂) |
|---|---|---|
|  (IXa) |  (IXb) wherein, Z is a suitable leaving group, e.g., F, Cl, Br, or I. | 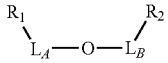 (IXc) |
|  (Xa) |  (Xb) + 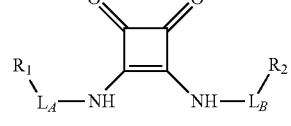 | 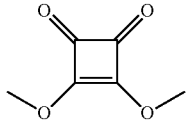 (Xc) |
|  (XIa) | 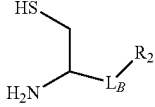 (XIb) | 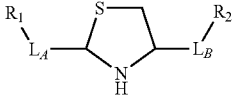 or 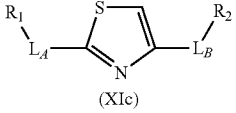 (XIc) |
|  (XIIa) | 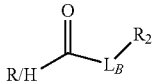 (XIIb) | 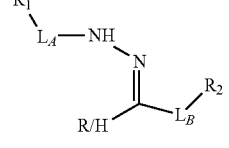 (XIIc) |
|  (XIIIa) |  (XIIIb) | 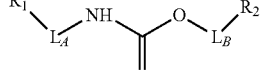 (XIIIc) |
| 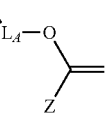 (XIVa) wherein, Z is a suitable leaving group, e.g., —OSu, —OBt, or —OAt | 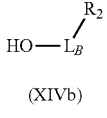 (XIVb) | 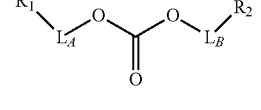 (XIVc) |

TABLE 1-continued

| $R_1$—$L_A$—$X_A$* | $X_B$—$L_B$—$R_2$* | $R_1$—$L_A$—X—$L_B$—$R_2$* (or $R_1$-Linker-$R_2$) |
|---|---|---|
|  (XVa) | 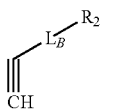 (XVb) | 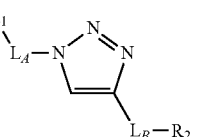 (XVc) |
|  (XVIa) | 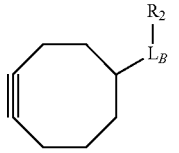 (XVIb) | 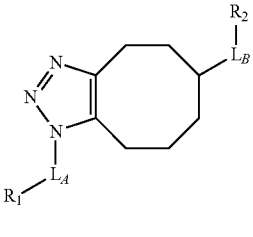 (XVIc) |
| 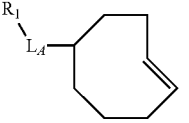 (XVIIa) | 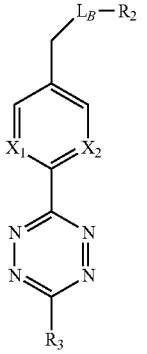 (XVIIb) wherein, $X_1$ and $X_2$ are atoms independently selected from C and N; and $R_3$ is a chemical group selected from the group consisting of: H, F, Cl, Br, I, $CH_3$, $CF_3$, $NH_2$, $NO_2$, OH, C(O)OH, C(O)OCH_3, $C(O)NH_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring. | 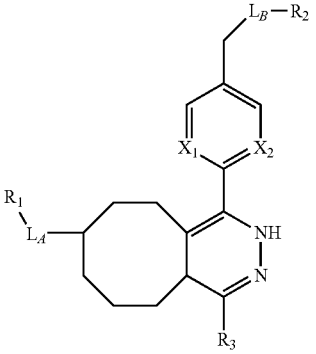 (XVIIc) wherein, $X_1$ and $X_2$ are atoms independently selected from C and N; and $R_3$ is a chemical group selected from the group consisting of: H, F, Cl, Br, I, $CH_3$, $CF_3$, $NH_2$, $NO_2$, OH, C(O)OH, C(O)OCH_3, $C(O)NH_2$, linear or branched ($C_2$-$C_5$) alkyl, linear or branched ($C_2$-$C_5$) alkenyl, linear or branched ($C_2$-$C_5$) alkynyl, unsubstituted or para-substituted 6-membered aryl ring, and unsubstituted or para-substituted 6-membered heteroaryl ring. |

*$R_1$ and $R_2$ are a tag and nucleoside-5'-oligophosphate, respectively, or $R_1$ and $R_2$ are a nucleoside-5'-oligophosphate and tag, respectively Table 1 exemplifies range of linkers and the corresponding reactive linker-forming groups that undergo a reaction that results in the covalent coupling linker. These various linkers and reactions are well-known in the art. The ordinary artisan will be able to identify the reagents needed for these reactions and either synthesize them or obtain them commercially. For example, reagents for conjugating or cross-linking polypeptide (or proteins) to other biomolecules can be used as linker forming groups to prepare the ion flow amplifying tagged nucleotide structures of the present disclosure. (See e.g., catalog of "crosslinking reagents" available from Thermo Scientific, USA at www.piercenet.com or Sigma-Aldrich, USA at www.sigmaaldrich.com). Similarly, terminal phosphate modified nucleosides and/or reagents for such modification with azide or alkyne groups (or other linker forming groups) are commercially available (see e.g., Jena Bioscience Gmbh, Jena, Germany). Additionally, a wide range of FMOC-protected amino acid residues modified with azide or alkyne groups (or other linker forming groups) that can be used in the automated solid-phase synthesis of polypeptides are commercially available (see e.g., AnaSpec, Fremont, Calif., USA).

It is contemplated that any of the pairs of linker forming groups of structural formulae (IVa)-(XVIIa) and (IVb)-(XVIIb) can be used in either configuration in preparing a linker useful in an ion flow amplifying tagged nucleotide compounds of the present disclosure (e.g., compound of formula (III)). That is, any of the linker forming groups, $X_A$ and $X_B$ can be used on either the tag or the nucleotide, as long as the linker forming groups are paired to provide the linker reaction forming the linker moiety X. Thus, any of the linker forming groups of structural formulae (IVa)-(XVIIa) could be attached to either the tag or the nucleotide, and the conjugate linker forming group of structural formulae (IVb)-(XVIIb) would be attached to the other. Thus, the groups $R_1$ and $R_2$ as depicted in the linkers of form $R_1$-$L_A$-X-$L_B$-$R_2$ in Table 1, can represent either the tag and the nucleotide, or the nucleotide and the tag, respectively. Accordingly, in some embodiments, the present disclosure provides ion flow amplifying tagged nucleotide compounds of formula (III), wherein the compound comprises a compound of formula $R_1$-$L_A$-X-$L_B$-$R_2$, wherein $R_1$ and $R_2$ are the nucleotide and the tag, or $R_1$ and $R_2$ are the tag and the nucleotide, respectively, and -$L_A$-X-$L_B$- comprises a chemical moiety selected from the moieties of structural formula (IVc)-(XVIIc) in Table 1.

As described above, the chemical moieties $L_A$ and $L_B$ which make up the linker can each independently comprise In one embodiment, the linker used in a tagged nucleotide compound the formula (III) is a linker in formula (XVc) comprising a triazole group X with moieties $L_A$ and $L_B$ on either side resulting in the linker of formula (XVd) shown below.

(XVd)

In some embodiments of the ion flow amplifying tagged nucleotide compounds of formula (III), the $L_A$ and $L_B$ chemical moieties comprise chemical moieties independently selected from the group consisting of moiety structures of formula (XVIIIa)-formula (XVIIId) as in Table 2.

TABLE 2

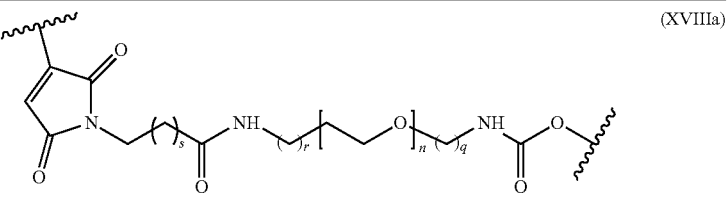

(XVIIIa)

wherein, n = 1 to 50, and q, r, and s each independently = 0, 1, 2, or 3;

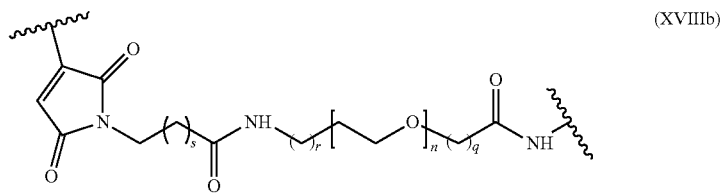

(XVIIIb)

wherein, n = 1 to 50, and q, r, and s each independently = 0, 1, 2, or 3;

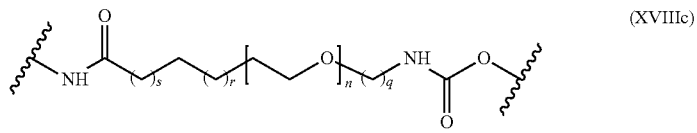

(XVIIIc)

wherein, n = 1 to 50, and q, r, and s each independently = 0, 1, 2, or 3;

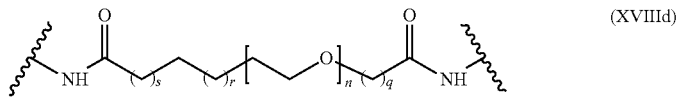

(XVIIId)

wherein, n = 1 to 50, and q, r, and s each independently = 0, 1, 2, or 3.

chemical moieties including linear ($C_1$-$C_{12}$) alkyl, ester, ether, thioether, amine, amide, imide, carbonate, carbamate, polyethylene glycol (PEG), and combinations thereof. Similar to the linker forming groups $X_A$ and $X_B$, it is contemplated that any of the chemical moieties $L_A$ and $L_B$, which make up the linker, can each independently be used with any of the linker forming groups, and can be used on either the tag or the nucleotide. Additionally, it is contemplated that the chemical moieties $L_A$ and $L_B$ can be the same or different.

Although Scheme 1 depicts the "-$L_B$-X-$L_A$-" linker that is formed as a moiety separate from the tag, it is contemplated that in some embodiments, the linker can be formed in a reaction with a linker forming group that can comprise part of the tag. For example, the tag can comprise an oligonucleotide wherein the oligonucleotide includes a monomer unit modified with a propargyl or other alkynyl group which can be covalently coupled to a desired nucleotide (or nucleotide analog) via an azide-alkyne "click" reaction. This propargyl group which could also be considered part of the tag can act as a linker forming group (i.e., "$X_B$") and undergoes a linker forming reaction with a linker forming group attached to a nucleotide.

Branched or Dendrimeric Linkers

In addition to the wide range of linkers having two reactive ends capable of covalent coupling to a plurality of molecular moieties, the ion flow amplifying tagged nucleotides of the present disclosure generally include at least one "branched" or "dendrimeric" linker, which is a type of linker moiety that has three or more reactive ends. The use of linkers comprising a branched or dendrimeric linker moiety facilitate the covalent coupling of a single tag to two or more nucleotides. The use of such linkers in tagged nucleotide compounds with improved properties as polymerase substrates are described in U.S. provisional appl. 62/342,796, filed May 27, 2016, entitled "Tagged Multi-Nucleotides Useful For Nucleic Acid Sequencing," which is hereby incorporated by reference herein.

Branched or dendrimeric linker moieties capable of providing three or more reactive ends that can be used in the tagged nucleotide compounds of the present disclosure are well-known in the art. See e.g., Shchepinov et al., "Oligonucleotide dendrimers: synthesis and use as polylabelled DNA probes," *Nucleic Acids Research*. 1997, Vol. 25, No. 22, 4447-4454. Branched or dendrimeric linker moieties providing three or more reactive ends useful in the compounds of the present disclosure are commercially available from various vendors of DNA synthesis reagents, e.g., Glen Research (Virginia, USA; www.glenresearch.com).

Accordingly, in some embodiments the ion flow amplifying tagged nucleotide compounds of the present disclosure (e.g., structural formula (I) and (II) can comprise a linker,

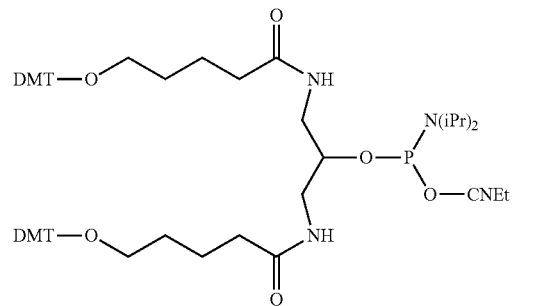

(19)

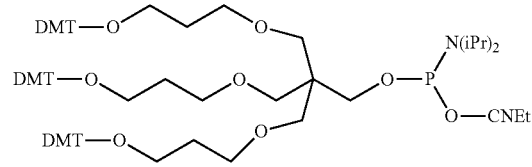

(20)

The branched or dendrimeric phosphoramidite "doubler" and "trebler" units of compounds (19) and (20) are easily attached to the end of oligonucleotide chains to generate a linker end on the oligonucleotide capable of attached 2 or more molecular moieties. Accordingly, an oligonucleotide comprising natural and/or non-natural monomer units can be used as a tag for ion flow amplifying tagged nucleotide.

In some embodiments of the present disclosure, the ion flow amplifying tagged nucleotide compound comprises a branched or dendrimeric "doubler" linker moiety and has a structural formula (IIIb):

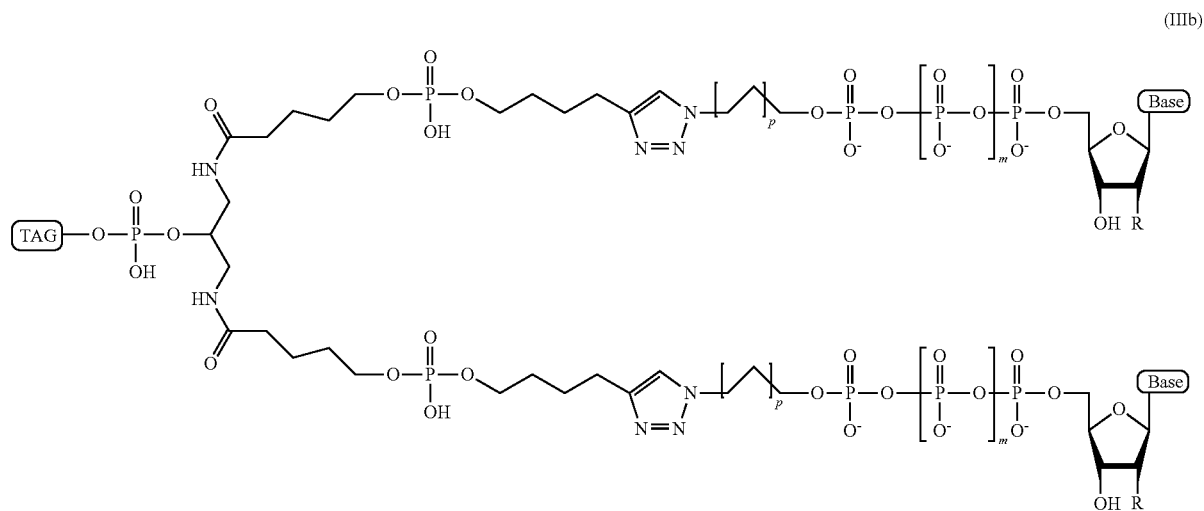

(IIIb)

wherein the linker comprises a branched or dendrimeric moiety capable of forming covalent linkages with three or more molecular moieties.

Exemplary reagents useful for preparing ion flow amplifying tagged nucleotide compound of the present disclosure wherein the linker comprises a branched or dendrimeric moiety include the protected phosphoramidite reagent compounds (19) and (20) shown below.

wherein, "Base" is a naturally occurring or non-naturally occurring nucleobase; R is selected from H and OH; m is from 2 to 12; p is from 2-10; and Tag is a tag comprising a negatively-charged polymer moiety which is capable of entering a nanopore and upon entering a nanopore in the presence of positive ions results in an increased flow of the positive ions through the nanopore.

In some embodiments of the present disclosure, the ion flow amplifying tagged nucleotide compound comprises a branched or dendrimeric "trebler" linker moiety and has a structural formula (IIIc):

(IIIc)

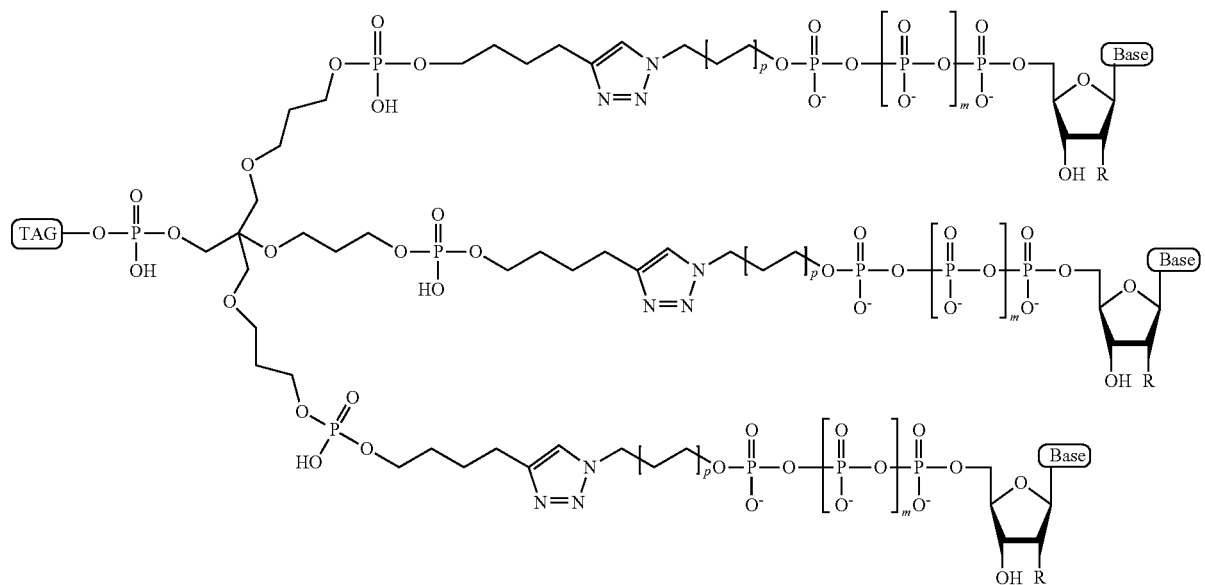

wherein, "Base" is a naturally occurring or non-naturally occurring nucleobase; R is selected from H and OH; m is from 2 to 12; p is from 2-10; and Tag is a tag comprising a negatively-charged polymer moiety which is capable of entering a nanopore and upon entering a nanopore in the presence of positive ions results in an increased flow of the positive ions through the nanopore.

Additionally, the branched or dendrimeric phosphoramidite "doubler" unit of compound (19) and the "trebler" unit of compound (20) can be easily combined to create linkers capable of covalent coupling a single molecular moiety (e.g., a tag) to 4, 6, 8, 9, 12, or more nucleotides. For example, a tag can be linked to compound (19) and then compound (20) via standard phosphoramidite synthesis methods to generate compound (21), which is capable of further linking to at least six additional molecular moieties, such as six nucleotides.

unit of compound (19) and a "trebler" unit of compound (20) may be covalently attached in a serial fashion to a "doubler" unit having DMT and Fmoc protecting groups that was previously attached to a single tag. Such a combination provides a single tag with a linker moiety capable of further linking to at least five additional molecular moieties, such as five nucleotides.

The ordinary artisan will immediately recognize that the branched or dendrimeric phosphoramidite units of compounds (19) and (20), or other such branched or dendrimeric linker moieties can be combined in numerous ways to generate ion flow amplifying tagged nucleotide compounds of the present disclosure.

Ion Flow Amplifying Tags

As noted elsewhere herein, prior known tag moieties used for nanopore detection upon entering a nanopore cause a decrease in positive ion flow through the nanopore which (21)

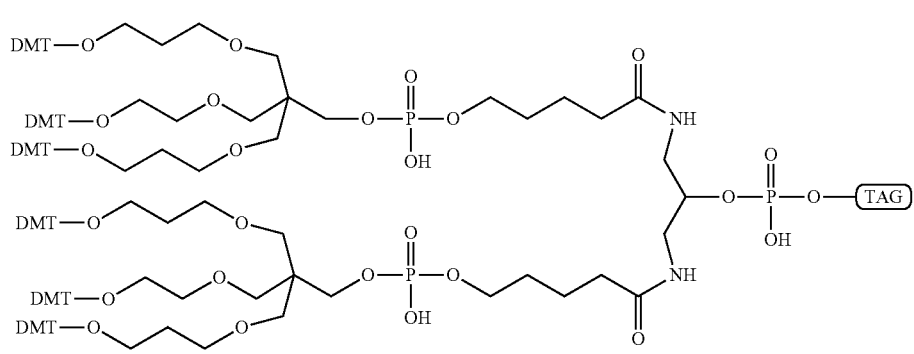

The three-ended phosphoramidite "doubler" unit of compound (19) can also be prepared (or commercially obtained) with one DMT protecting group and one FMOC protecting group. This "doubler" unit with two different protecting groups can then be used to attach subsequently two different branched or dendrimeric units. For example, a "doubler"

results in "blocking" current signal measured across the nanopore that is below the O.C. signal. The tag moieties of the present disclosure upon entering a nanopore result in the surprising technical effect of an increased flow of the positive ions through the nanopore. This increased flow of positive ions results in a measured tag current signal across the nanopore that is above the O.C. signal of the nanopore without any tag present. Thus, the ion flow amplifying tag moieties disclosed herein do not result in a "blocking" current signal but an ion flow amplifying tag current signal. This surprising technical effect of ion flow amplification opens up a whole new range nanopore detectable signals above the O.C. signal. In this detection range there generally is less background noise than the range below O.C. signal. Thus, the ion flow amplifying tags exhibit the advantages of both increasing the dynamic range to both above and below the O.C. signal, and providing higher sensitivity due to lower background noise in detecting the tag current signals in this range. Accordingly, in some embodiments of the ion flow amplifying tags useful in the compounds and tagged nucleotides of the present disclosure, the increased positive ion flow results in a measured current across the nanopore that is greater than O.C. current, optionally at least 5% greater than O.C. current, at least 10% greater than O.C. current, at least 25% greater than O.C. current, or at least 50% greater than O.C. current.

Generally, the structures of the ion flow amplifying tags of the present disclosure comprise a negatively-charged polymer moiety which is capable of entering a nanopore and upon entering a nanopore in the presence of positive ions results in an increased flow of the positive ions through the nanopore. Without intending to be bound by a proposed mechanism, it is believed that the long, extended, thin polyanionic structure of such tags is able to rapidly bind numerous positive ions on the ds side of a nanopore device and then as the tag is pulled into the nanopore by an applied potential it effectively delivers the positive ions to the trans side of the device—more quickly than they can move through the nanopore by themselves.

As noted above, the ion flow amplifying tag moieties should have structures comprising a negatively charged polymer that can adopt a narrow, elongated, rod-like conformation in aqueous solution, and which has a molecular length capable of approximately spanning the length of the nanopore. Generally, a standard DNA strands has 3.4 nm (or 34 angstroms) per 10 nucleotides, or a molecular length of about 102 angstroms per 30 nucleotides. The natural nucleotide T has a molecular diameter of about 18 angstroms, whereas a non-natural abasic nucleotide such as "Sp2," "Sp3," "dSp," (also referred to in the oligonucleotide synthesis art as a "spacer") has a narrower molecular diameter of about 10 angstroms (or less).

Accordingly, ion flow amplifying tags useful in the compounds and tagged nucleotides of the present disclosure, generally comprise a negatively-charged polymer moiety that has a molecular length of about 80 angstroms to about 250 angstroms, and a molecular diameter of about 8 angstroms to about 18 angstroms. In some embodiments, the tagged nucleotides comprise a negatively-charged polymer moiety that has a molecular length of between about 80 angstroms and about 250 angstroms, and a molecular diameter of less than about 15 angstroms, optionally, a molecular diameter of less than about 12 angstroms, or less than about 10 angstroms.

The ion flow amplifying tags of the present disclosure have negative charges distributed regularly along their length to allow suitably efficient transport of positive ions through the nanopore. Accordingly, in some embodiments the ion flow amplifying tags useful in the compounds and tagged nucleotides of the present disclosure, generally comprise a negatively-charged polymer moiety, wherein the negatively-charged polymer moiety has at least one negative charge per 10 angstroms of molecular length, optionally at least one negative charge per 7.5 angstroms of molecular length, or at least one negative charge per 3.5 angstroms of molecular length.

The density of negative charge on the ion flow amplifying tag structure can alternatively be described in term of negative charge per number of atoms in the polymer chain. Thus, in some embodiments the ion flow amplifying tags useful in the compounds and tagged nucleotides of the present disclosure comprises a negatively-charged polymer moiety comprising a covalently linked chain of from 150 to 900 atoms with a negatively charged group attached to an atom of the chain at an interval of every 3 to 20 atoms, optionally an interval of every 3 to 10 atoms. In some embodiments, the covalently linked chain of from 150 to 900 atoms comprises chemical groups selected from phosphodiester, peptide, ester, ether, alkyl, alkenyl, alkynyl, perfluorinated alkyl, and any combination thereof. In some embodiments, the negatively charged group is selected from group consisting of phosphate, phosphonate, phosphorothioate, sulfate, sulfonate, carboxylate, and any combination thereof.

Generally, the overall negative charge of the ion amplifying tag can be varied based on the length and charge distribution over the length of the tag. Such parameters can be varied in order to alter the tag current signal. In some embodiments of the ion flow amplifying tags useful in the compounds and tagged nucleotides of the present disclosure the negatively-charged polymer moiety has an overall negative charge of from (−20) to (−60), optionally, an overall negative charge of from (−25) to (−50), optionally, an overall negative charge of from (−30) to (−40), or optionally an overall negative charge of from (−31) to (−37).

The ion flow amplifying tags generally comprise a negatively charged polymer structure. That polymeric structure can be further described in terms of the number and type of its constituent monomer units. Generally, monomer units useful in the negatively charged polymer moiety of the tags of the present disclosure comprise a negatively-charged group attached to a covalently linked chain of from 3 to 20 atoms, optionally a chain of from 3 to 10 atoms. Accordingly, in some embodiments of the ion flow amplifying tags useful in the compounds and tagged nucleotides of the present disclosure the negatively-charged polymer moiety comprises a covalently linked chain of from 10 to 60 monomer units, optionally from 20 to 50 monomer units, optionally from 25 to 40 monomer units, or optionally from 27 to 35 monomer units.

Generally, the monomer units are described in terms of their covalent linking structure within the polymer moiety. Accordingly, in some embodiments the monomer units of the polymer moiety comprise covalent links selected from the group consisting of phosphodiester, peptide, ester, ether, alkyl, alkenyl, alkynyl, perfluoroalkyl, and any combination thereof. In some embodiments, the monomer units comprise a negatively charged group selected from the group consisting of phosphate, sulfate, carboxylate, and any combination thereof.

Specific monomer units useful as constituents of the negatively charged polymer moiety of the ion flow amplifying tags of the present disclosure are provided in Table 3. Accordingly, in some embodiments the ion flow amplifying tags useful in the compounds and tagged nucleotides of the present disclosure comprises a negatively-charged polymer moiety comprises monomer units, wherein the monomer units are independently selected from the group consisting of the structures of formula (1a), (1b), (1c), (1d), (1e), (1f), (1g), (1h), (1i), (1j), (1k), (1l), (1m), (2a), (2b), (2c), (3a), (3b), (3c), and any combination thereof.

TABLE 3
| Monomer Units | |
|---|---|
| 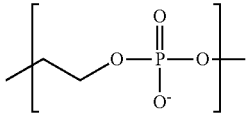 | (1a) |
| 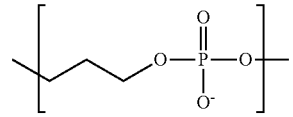 | (1b) |
| 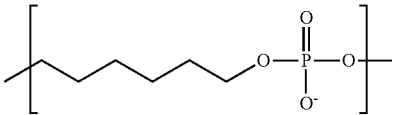 | (1c) |
| 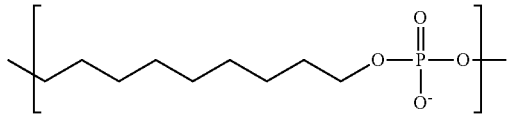 | (1d) |
| 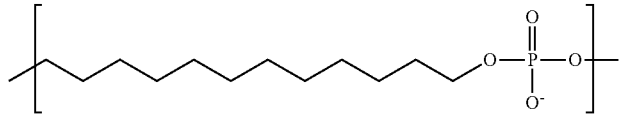 | (1e) |
| 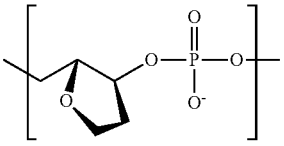 | (1f) |
| 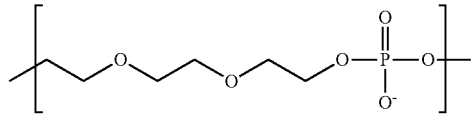 | (1g) |
| 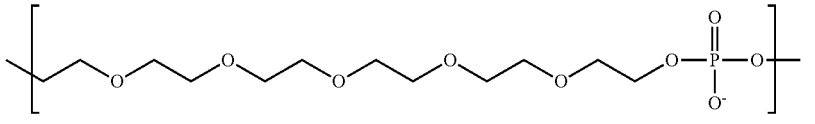 | (1h) |
| 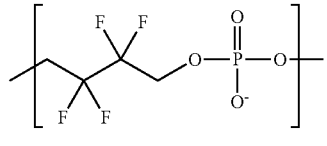 | (1i) |
| 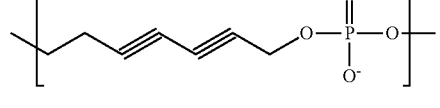 | (1j) |
| 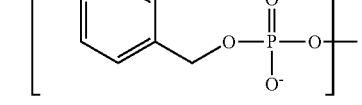 | (1k) |

TABLE 3-continued

| Monomer Units | |
|---|---|
| [structure: phenylene with ethyl linkers and phosphate group] | (1l) |
| [structure: phenylene with alkyne linkers and phosphate group] | (1m) |
| [structure: amide with carboxylate side group] | (2a) |
| [structure: amide with carboxylate side group variant] | (2b) |
| [structure: amide with carboxylate side group variant] | (2c) |
| [structure: backbone with carboxylate pendant] | (3a) |
| [structure: backbone with sulfonate pendant] | (3b) |
| [structure: backbone with sulfonate pendant variant] | (3c) |

Oligonucleotide Tags

As noted in the Background and elsewhere herein, a wide range of oligonucleotide have been prepared and used tag moieties for nanopore detection. These prior known oligonucleotide tags, however, are known only to produce tag current signals below O.C. signal indicating that they result in a decrease in positive ion flow. The present disclosure provides oligonucleotide tags that are capable of amplifying ion flow. Generally, the ion flow amplifying oligonucleotide tags comprise polymers of 25 to 35 monomer units which are non-natural abasic nucleotide analog structures. These amidite reagent are easily synthesized into polymers via standard automated amidite coupling chemistry, and used to prepare ion flow amplifying tagged nucleotides of the present disclosure. Such monomer unit structures are shown in Table 3 as structures of formula (1a), (1b), (1c), (1d), (1e), (1f), (1g), (1h), (1i), (1j), (1k), (1l), and (1m). Thus, in some embodiments, the ion flow amplifying tags useful in the compounds and tagged nucleotides of the present disclosure comprise a negatively-charged polymer, wherein the polymer comprises monomer units selected from the structures of formula (1a), (1b), (1c), (1d), (1e), (1f), (1g), (1h), (1i), (1j), (1k), (1l), (1m), and any combination thereof.

The monomer structures comprising phosphodiester linkages of Table 3, and a wide variety of other such non-natural abasic nucleotide analogs (often also referred to as spacer units) are available commercially in amidite reagent form (e.g., phosphoramidite or phosphonamidite) (from e.g., Glen Research, 22825 Davis Drive, Sterling, Va., USA). It is contemplated that additional ion flow amplifying tags comprising this range of phosphodiester linked monomer units can be used prepared using these amidite reagents and standard automated amidite synthesis methods.

Amidite reagents corresponding to the monomer units with phosphodiester linkages of Table 3 can be used to prepare an ion flow amplifying tag having a polymeric structure via standard amidite coupling chemistry. That is, each of the phosphoramidite (or phosphonamidite) reagents will react in an amidite coupling reaction with a nucleotide polymer (e.g., oligonucleotide) to insert a monomer unit with its particular structure into the polymer. This resulting polymeric structure will have phosphate (or phosphonate) linkage to the adjacent monomer units in the polymer. Such polymers can then be used to prepare an ion flow amplifying tagged nucleotide of the present disclosure via linking chemistry disclosed herein, and well-known to the skilled artisan. Accordingly, the present disclosure provides an ion flow amplifying tagged nucleotide compound (e.g., having structural formula (I), (II), or (III)), wherein the tag comprises a negatively charged polymeric structure having at least one monomer unit resulting from the reaction of an amidite reagent corresponding to a monomer unit of Table 3.

Generally, in any of the embodiments of ion flow amplifying tagged nucleotide compounds disclosed herein, the Tag can comprise an oligonucleotide of at least 10-mer, 15-mer, 20-mer, 25-mer, 30-mer, 35-mer, 40-mer, 50-mer, 60-mer or more monomer units in length; optionally, wherein the oligonucleotide comprises monomer units selected from Table 3.

The ordinary artisan will recognize that some of the monomer units disclosed in Table 3 are also referred to in commercial oligonucleotide synthesis catalogs as "spacers" (e.g., "SpC3", "dSp"). The ordinary artisan will also recognize that some of the oligonucleotide tags described herein (including in the Examples) are referred to using well-known oligonucleotide synthesis nomenclature (see e.g., the web-site of Integrated DNA Technologies at www.idtdna.com for further description of commonly used oligonucleotide synthesis nomenclature). For example, in the context of the oligonucleotide embodiments disclosed elsewhere herein, the phosphodiester linked monomer unit structures of Table 3, structures of formula (1a), (1b), (1c), (1d), (1e), (1f), (1g), (1h), (1i), (1j), (1k), (1l), and (1m), are referred to herein by the oligonucleotide synthesis related names of Table 4.

TABLE 4

| Oligonucleotide Monomer Unit Structure | Oligonucleotide Synthesis Related Name of Monomer Unit |
|---|---|
| (1a) | SpC2 |
| (1b) | SpC3 |
| (1c) | SpC6 |
| (1d) | SpC9 |
| (1e) | SpC12 |
| (1f) | dSp |

TABLE 4-continued

| Oligonucleotide Monomer Unit Structure | Oligonucleotide Synthesis Related Name of Monomer Unit |
|---|---|
| (1g) | Sp9 |
| (1h) | Sp18 |
| (1i) | SpC4-F4 |
| (1j) | SpC7-Pra2 |
| (1k) | SpC6-Bz |
| (1l) | BHEB |
| (1m) | S500 |

In some embodiments, the present disclosure provides an ion flow amplifying tagged nucleotide compound (e.g., of structural formula (I), (II), or (III)), wherein the negatively-charged polymer moiety comprises an oligonucleotide of formula $(A)_m\text{-}(B)_n\text{-}(C)_p\text{-}(D)_q$, wherein A, B. C, and D, are monomer units independently selected from the monomer unit structures of formula (1a), (1b), (1c), (1d), (1e), (1f), (1g), (1h), (1i), (1j), (1k), (1l), and (1m), and each of m, n, p, and q is from 0 to 40, and m+n+p+q is from 10 to 40, optionally m+n+p+q is from 20 to 40, m+n+p+q is from 25 to 35, or m+n+p+q is from 27 to 35.

In some embodiments, the present disclosure provides an ion flow amplifying tagged nucleotide compound (e.g., of structural formula (I), (II), or (III)), wherein the negatively-charged polymer moiety comprises an oligonucleotide of formula $(A)_n$, wherein A is a monomer unit independently selected from the monomer unit structures of formula (1a), (1b), (1c), (1d), (1e), (1f), (1g), (1h), (1i), (1j), (1k), (1l), and (1m), and n is from 10 to 40, optionally n is from 20 to 40, n is from 25 to 35, or n is from 27 to 35.

In some embodiments, the present disclosure provides an ion flow amplifying tagged nucleotide compound (e.g., of structural formula (I), (II), or (III)), wherein the negatively-charged polymer moiety comprises an oligonucleotide selected from Table 5.

TABLE 5

Exemplary Negatively-Charged Polymer Moieties (Oligonucleotides)

-TT-(SpC2)$_{28}$-(SEQ ID NO: 1)
-TT-(SpC3)$_{28}$-(SEQ ID NO: 2)
-(SpC3)$_{31}$-(SEQ ID NO: 3)
-TT-(dSp)$_{26}$-TT-(SEQ ID NO: 4)
-TT-(SpC4-F4)$_{28}$-(SEQ ID NO: 5)
-TT-(SpC7-Pra2)$_{28}$-(SEQ ID NO: 6)
-(SpC2)$_8$-T$_6$-(SpC2)$_{16}$-(SEQ ID NO: 12)
-(SpC2)$_8$-(N3CEdT)$_7$-(SpC2)$_{15}$-(SEQ ID NO: 13)
-(SpC2)$_6$-TT-(BHEB)-T-(SpC2)$_{20}$-(SEQ ID NO: 14
-(SpC2)$_9$-T-(BHEB)$_2$-T-(SpC2)$_{17}$-(SEQ ID NO: 15)
-(SpC2)$_8$-(S500)$_3$-(SpC2)$_{17}$-(SEQ ID NO: 16)

Ion flow amplifying tagged nucleotide compounds, wherein the tag comprises an oligonucleotide include compounds also are disclosed and exemplified in the Examples.

The exemplary negatively charged polymer moieties useful as ion flow amplifying compounds generally have molecular lengths of about 80 angstroms to about 150 angstroms, and molecular diameters of less than about 15 angstroms.

It is contemplated that the negatively-charged polymer moiety comprising an oligonucleotide can further comprise a 3' end group. Such 3' end groups are known to act to protect the tag from digestion in the presence of polymerase enzymes. See e.g., protective 3' end groups as disclosed in WO 2015/148402. Exemplary 3' end groups useful in the ion flow amplifying tags of the present disclosure include propanol ("C3") and biotin, however, the ordinary artisan will recognize that numerous other groups are available.

The present disclosure provides the ordinary artisan with tools to prepare ion flow amplifying tagged nucleotides with tag moieties that provide ion flow amplification characteristics useful across a wide range of nanopore devices and detection systems.

Methods of Preparing Ion Flow Amplifying Tagged Nucleotides

Standard synthetic methods can be used in preparing the ion flow amplifying tagged nucleotide compounds of the present disclosure (e.g., compounds of structural formulas (I), (II), (III)). The standard azido-alkyne click reaction is described above (e.g., compounds of (XIX), (XX), (XXI), or (XXII)) and in the Examples. Tables 1 and 2 illustrate a range of linkers and linker forming group reactions that can be used in preparing the ion flow amplifying tagged nucleotides of the present disclosure. In one embodiment, any of the linker forming groups of structural formulas (IVa)-(XVIIa) shown in Table 1 can be attached to a branched or dendrimeric linker attached to a tag, or to a terminal phosphate of a nucleotide, and the corresponding conjugate linker forming group of structural formulae (IVb)-(XVIIb) would be attached to other. The resulting covalent linker structures forming the multi-nucleotide-oligophosphate-linker-tag compound are exemplified by structural formulae (IVc)-(XVIIc) in Table 1. The covalent linkage structure and include the dihydropyrazidine group structure (XVIIc) that results from the click reaction of trans-cyclooctene (XVIIa) and tetrazine (XVIIb) linker forming groups.

Accordingly, the present disclosure provides a method of preparing a ion flow amplifying tagged nucleotide comprising: (a) providing (i) a nucleotide with from 3 to 12 phosphates attached to its 5'-position, wherein the terminal phosphate is coupled to a first linker forming group (e.g., $X_A$ or $X_B$); and (ii) an ion flow amplifying tag, wherein the tag is coupled to a second linker forming group (e.g., $X_B$ or $X_A$) that is capable of reacting with the first linker forming group to form a linker (e.g., -X-); and (b) reacting the first linker forming group with the second linker forming group to form the ion flow amplifying tagged nucleotide. First and second linker forming groups that are capable of reacting to form a linker are exemplified in Table 1 above. Thus, in some embodiments of the method, the first linker forming group is selected from the compounds of structural formulas (IVa)-(XVIIa) and the second linker forming group is the corresponding reactive compound of structural formulas (IVb)-(XVIIb); or alternatively, the first linker forming group is selected from the compounds of structural formulas (IVb)-(XVIIb) and the second linker forming group is the corresponding reactive compound of structural formulas (IVa)-(XVIIIa).

In some embodiments, the disclosure provides method of preparing the ion flow amplifying tagged nucleotide compound of structural formula (II)

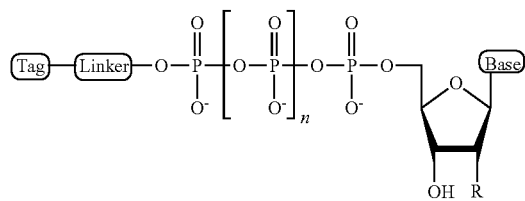

(II)

wherein, Base is selected from adenosine, cytidine, guanosine, thymidine, and uridine; R is selected from H and OH; n is from 1 to 4; Linker is a linker comprising a covalently bonded chain of 2 to 100 atoms; m is from 2 to 12; and Tag is an ion flow amplifying tag comprising a negatively-charged polymer moiety which is capable of entering a nanopore and upon entering a nanopore in the presence of positive ions results in an increased flow of the positive ions through the nanopore; and the method comprises the steps of:

(a) providing (i) a nucleotide with from 3 to 12 phosphates attached to its 5'-position, wherein the terminal phosphate is coupled to a first linker forming group; and (ii) an ion flow amplifying tag, wherein the tag comprises a molecular moiety which is capable of producing a detectable signal, comprising at least a second linker forming group capable of reacting with the first linker forming group to form a covalent linker between the nucleotide and the tag; wherein (1) the first linker forming group is selected from the compounds of structural formulas (IVa)-(XVIIIa) and the second linker forming group is the corresponding reactive compound of structural formulas (IVb)-(XVIIb); or (2) the first linker forming group is selected from the compounds of structural formulas (IVb)-(XVIIb) and the second linker forming group is the corresponding reactive compound of structural formulas (IVa)-(XVIIIa);

and (b) reacting the first linker forming group with the second linker forming group, thereby forming a covalent linkage between the nucleotide and ion flow amplifying tag.

In some embodiments of the methods of preparing the ion flow amplifying tagged nucleotide compound, the first linker forming group attached to the terminal phosphate is an azide group and the second linker forming group attached to the tag is an alkyne. In other embodiments, the first linker forming group attached to the terminal phosphate is an alkyne group and the second linker forming group attached to the tag is an azide.

In some embodiments of the methods of preparing the ion flow amplifying tagged nucleotide, the first linker forming group attached to the terminal phosphate is a tetrazine and the second linker forming group attached to the tag is a trans-cyclooctene. In other embodiments, the first linker forming group attached to the terminal phosphate is a trans-cyclooctene and the second linker forming group attached to the tag is a tetrazine.

As described elsewhere herein, in some embodiments of the methods of preparing tagged nucleotides, a branched or dendrimeric linker structure can be used to form a multi-nucleotide tagged with a single ion flow amplifying tag. For example, the linker structure can be generated using the doubler or trebler linker units of compounds (19) or (20). In some embodiments, the doubler or trebler linker units can be linked in a serial fashion to generate branched or dendrimeric linkers have four or more reactive linker forming groups available (e.g., as in compound (21)).

Use of Tagged Nucleotides in Nanopore Sequencing

The ion flow amplifying tagged nucleotide compounds of the present disclosure can be used in the known nanopore sequencing methods wherein a nanopore detects the presence of a tag attached to a complementary nucleotide as it is incorporated (or after it is incorporated and released) by a strand-extending enzyme (e.g., polymerase, ligase) located proximal to the nanopore and which is extending a primer complementary of a target nucleic acid sequence. General methods, materials, devices, and systems for carrying out nanopore sequencing using tagged nucleotides are described in US Pat. Publ. Nos. 2013/0244340 A1, 2013/0264207 A1, 2014/0134616 A1, 2015/0119259 A1, and U.S. Ser. No. 14/666,124, filed Mar. 23, 2015, each of which is hereby incorporated by reference herein. The ion flow amplifying tagged nucleotides of the present disclosure can be employed in these general methods for using tagged-nucleotides for nanopore sequencing of nucleic acids. Indeed, as illustrated in the Examples herein, the ion flow amplifying tagged nucleotide compounds of the present disclosure have the improved characteristic of increasing ion flow and resulting in nanopore detectable tag currents above the open channel (O.C.) current of the nanopore along. These above O.C. signals are in a detection range that exhibits lower noise and thereby allow for more accurate sequence reads in nanopore sequencing than the corresponding non-ion-flow amplifying tagged nucleotide compounds.

Thus, in one embodiment, the present disclosure provides a method for determining the sequence of a nucleic acid comprising: (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase; (b) contacting the nanopore sequencing composition with (i) a strand of the nucleic acid; and (ii) a set of compounds each comprising a different nucleoside-5'-oligophosphate moiety covalently linked to a tag, wherein each member of the set of compounds has a different tag which results in a different flow of positive ions through a nanopore when the tag enters the nanopore, and at least one of the different tags comprises a negatively-charged polymer moiety which upon entering a nanopore in the presence of positive ions results in an increased flow of the positive ions through the nanopore; and (c) detecting the different flows of positive ions resulting from the entry of the different tags in the nanopore over time and correlating to each of the different compounds incorporated by the polymerase which are complementary to the nucleic acid sequence, and thereby determining the nucleic acid sequence.

In some embodiments, the present disclosure provides a method for determining the sequence of a nucleic acid comprising: (a) providing a nanopore sequencing composition comprising: a membrane, an electrode on the cis side and the trans side of the membrane, a nanopore with its pore extending through the membrane, an electrolyte solution in contact with both electrodes, an active polymerase situated adjacent to the nanopore, and a primer strand complexed with the polymerase; (b) contacting the nanopore sequencing composition with (i) a strand of the nucleic acid; and (ii) a set of tagged nucleotides each with a different tag, wherein each different tag causes a different tag current level across the electrodes when it is situated in the nanopore, and the set comprises at least one compound of structural formula (I)

N-P-L-T (I)

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; m is from 2 to 12 and indicates the number of N-P-L moieties; and T is a ion flow amplifying tag covalently attached the N-P-L moieties, wherein the tag comprises a negatively-charged polymer moiety which upon entering a nanopore in the presence of positive ions results in an increased flow of positive ions through the nanopore; and (d) detecting the flow of positive ions through the nanopore by detecting current levels across the electrodes over time and correlating to each of the different tagged nucleotides incorporated by the polymerase which are complimentary to the nucleic acid sequence, and thereby determining the nucleic acid sequence.

In some embodiments of the method for determining the sequence of a nucleic acid, the set of tagged nucleotides each with a different tag, comprises at least one ion flow amplifying tagged compound that comprises a structure of formula (II):

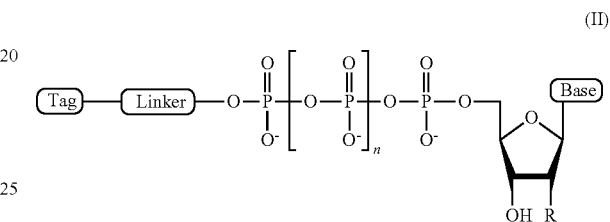

wherein, Base is selected from adenosine, cytidine, guanosine, thymidine, and uridine; R is selected from H and OH; n is from 1 to 4; Linker is a linker comprising a covalently bonded chain of 2 to 100 atoms; m is from 2 to 12; and Tag is a tag comprising a negatively-charged polymer moiety which is capable of entering a nanopore and upon entering a nanopore in the presence of positive ions results in an increased flow of the positive ions through the nanopore.

When used in the methods for determining the sequence of a nucleic acid the ion flow amplifying tagged nucleotide compounds comprising structures of formula (I) or (II) can include any of the ranges of compound embodiments disclosed elsewhere herein. For example, the nucleoside (N) of formula (I) can be any nucleoside capable of being incorporated by a strand-extending enzyme, such as a polymerase, when the nucleoside is covalently coupled to an oligophosphate (P), such as a triphosphate; and the nucleoside can comprise a naturally occurring or non-naturally occurring nucleobase, and a naturally occurring or non-naturally occurring sugar moiety, such as a ribose or deoxyribose group.

Sets of Tagged Nucleotides

As described elsewhere herein, methods for determining the sequence of a nucleic acid using nanopore detection generally require a set of tagged nucleotide compounds each capable of being a substrate for a strand-extending enzyme and each comprising a different tag associated with a nucleotide that is desired to be detected. In standard embodiments for sequencing DNA strands, the method requires a set of at least the four standard deoxy-nucleotides dA, dC, dG, and dT, wherein each different nucleotide is attached to a different tag capable of being detected upon the nucleotide being incorporated by a proximal strand extending enzyme, and furthermore wherein the each tag's nanopore detectable signal (e.g., tag current) is distinguishable from the nanopore detectable signals of each of the other three tags, thereby allowing identification of the specific nucleotide incorporated by the enzyme. Generally, each of the different tagged nucleotides in a set is distinguished by the distinctive detectable signal the tag produces when it is incorporated into a new complementary strand by a strand-extending enzyme.

Among the detectable signal characteristics, alone or in combination, that can be used to distinguish the tagged nucleotides in a nanopore detection method is the change in ion flow caused by the presence of the tag in the nanopore, which in turn results in a change in the current level measure across the electrodes of the nanopore detection system (under either DC or AC potential). Accordingly, in some embodiments, the present disclosure provides a set of tagged nucleotides each with a different tag, wherein each different tag causes a different ion flow through the pore resulting in a different detectable tag current level across the electrodes when it is situated in the nanopore, and the set comprises at least one compound of structural formula (I)

N-P-L-T    (I)

wherein, N is a nucleoside; P is an oligophosphate covalently attached to a 5'-O group of the nucleoside, wherein the oligophosphate consists of 3 to 12 phosphate groups; L is a linker covalently attached to a terminal phosphate group of the oligophosphate; m is from 2 to 12 and indicates the number of N-P-L moieties; and T is a tag covalently attached the N-P-L moieties, T is a ion flow amplifying tag covalently attached the N-P-L moieties, wherein the tag comprises a negatively-charged polymer moiety which upon entering a nanopore in the presence of positive ions results in an increased flow of positive ions through the nanopore.

In some embodiments of the set of ion flow amplifying tagged nucleotides each with a different tag, the set comprises at least one compound that comprises a structure of formula (II):

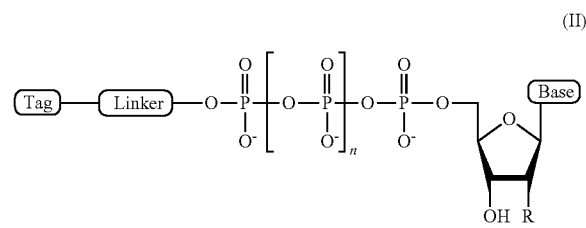

(II)

wherein, Base is selected from adenosine, cytidine, guanosine, thymidine, and uridine; R is selected from H and OH; n is from 1 to 4; Linker is a linker comprising a covalently bonded chain of 2 to 100 atoms; m is from 2 to 12; and Tag is a tag comprising a negatively-charged polymer moiety which is capable of entering a nanopore and upon entering a nanopore in the presence of positive ions results in an increased flow of the positive ions through the nanopore.

It is contemplated that the ion flow amplifying tagged nucleotides of the present disclosure may be used in sets of tagged nucleotides that also include tagged nucleotides that block rather than amplify ion flow through the nanopore, and/or sets with tagged nucleotides having different types of tags, such as both oligonucleotide tags and polypeptide tags. For example, in some embodiments, the set of ion flow amplifying tagged nucleotides can comprise an ion flow amplifying tagged nucleotide of structural formula (I), (II), or (III), and the other tagged nucleotides in the set can comprise nucleotides attached to oligonucleotide tags that do not amplify ion flow and which result in tag current signal below the nanopore O.C. signal level. Such oligonucleotide-tagged nucleotides that result in tag current signal below the nanopore O.C. signal levels are known in the art and can be used in sets along with the ion flow amplifying tagged nucleotides disclosed herein. (See e.g., US Pat. Publ. Nos. 2013/0244340 A1, 2013/0264207 A1, 2014/0134616 A1, 2015/0119259 A1, and U.S. Ser. No. 14/666,124, filed Mar. 23, 2015, each of which is hereby incorporated by reference herein).

Alternatively, in some embodiments, a set tagged nucleotides can include ion flow amplifying tagged nucleotides from across a range of negatively charge polymer moiety structures, such as those available using the monomer units of Table 3—e.g., an oligonucleotide tag, a polypeptide tag, and/or a polyethylene glycol tag.

In some embodiments, the set of tagged nucleotides comprises at least two, at least three, or at least four ion flow amplifying tagged nucleotide compounds of structural formula (I), (II), or (III) wherein each of the different tags of the at least two, at least three, or at least four of the ion flow amplifying tagged nucleotide compounds in the set produces a nanopore detectable signal that is distinguishable from the others in the set. Methods and techniques for determining the nanopore detectable signal characteristics, such as tag current and/or dwell time, are known in the art. (See e.g., US Pat. Publ. Nos. 2013/0244340 A1, 2013/0264207 A1, 2014/0134616 A1, 2015/0119259 A1, and U.S. Ser. No. 14/666,124, filed Mar. 23, 2015, each of which is hereby incorporated by reference herein.) Such methods include nanopore sequencing experiments under AC voltage potentials using a nanopore array as described in the Examples herein.

Accordingly, in some embodiments, the present disclosure provides a set of tagged nucleotides comprising at least two different ion flow amplifying tagged nucleotides each having a different tag, wherein the at least two different tags exhibit distinguishable levels of amplified positive ion flow resulting different measurable tag current levels above the nanopore O.C. current level. In some embodiments, the at least two different ion flow amplifying tagged nucleotides comprise a compound of structure (I), structure (II), or structure (III). In some embodiments, the at least two different ion flow amplifying tagged nucleotides each comprises a different negatively charged polymer moiety, optionally, each polymer moiety comprising a different sequence of monomer units selected from Table 3 of Table 4. In some embodiments, the at least two different tags exhibit tag current levels above O.C. current level that differ by at least 10%, at least 25%, at least 50%, or at least 75%. The measurement of the difference between tag current levels can be made using any suitable nanopore detection method. For example, the tag current levels of each of the at least two different ion flow amplifying tagged nucleotides can be measured in a nanopore sequencing experiment, as is generally described in the Examples herein.

In some embodiments, the at least two different ion flow amplifying tagged nucleotides comprise the following set of four tagged nucleotide compounds: dA6P-(Linker)-$T_{30}$-C3; dC6P-(Linker)-TT-$(dSp)_{26}$-TT-C3; dG6P-(Linker)-TT-$(SpC2)_{28}$-biotin; and dT6P-(Linker)-TT-$(SpC3)_{28}$-biotin; wherein, "(Linker)" refers to a linker of formula (XVd) (see above).

Nanopore Devices

Nanopore devices and methods for making and using them in nanopore detection applications, such as nanopore sequencing using ion flow amplifying tagged nucleotides of the present disclosure, are known in the art (See e.g., U.S. Pat. Nos. 7,005,264 B2; 7,846,738; 6,617,113; 6,746,594; 6,673,615; 6,627,067; 6,464,842; 6,362,002; 6,267,872; 6,015,714; 5,795,782; and U.S. Publication Nos. 2015/

0119259, 2014/0134616, 2013/0264207, 2013/0244340, 2004/0121525, and 2003/0104428, each of which are hereby incorporated by reference in their entirety). Nanopore devices useful for measuring nanopore detection are also described in the Examples disclosed herein. Generally, the nanopore devices comprise a pore-forming protein embedded in a lipid-bilayer membrane, wherein the membrane is immobilized or attached to a solid substrate which comprises a well or reservoir. The pore of the nanopore extends through the membrane creating a fluidic connection between the as and trans sides of the membrane. Typically, the solid substrate comprises a material selected from the group consisting of polymer, glass, silicon, and a combination thereof. Additionally, the solid substrate comprises adjacent to the nanopore, a sensor, a sensing circuit, or an electrode coupled to a sensing circuit, optionally, a complementary metal-oxide semiconductor (CMOS), or field effect transistor (FET) circuit. Typically, there are electrodes on the as and trans sides of the membrane that allow for a DC or AC voltage potential to be set across the membrane which generates a baseline current flow (or O.C. current level) through the pore of the nanopore. The presence of a tag, such as an ion flow amplifying tag of the present disclosure, results in change in positive ion flow through the nanopore and thereby generates a measurable change in current level across the electrodes relative to the O.C. current of the nanopore.

It is contemplated that the ion flow amplifying tag compounds of the present disclosure can be used with a wide range nanopore devices comprising nanopores generated by both naturally-occurring, and non-naturally occurring (e.g., engineered or recombinant) pore-forming proteins. A wide range of pore-forming proteins are known in the art that can be used to generate nanopores useful for nanopore detection of the ion flow amplifying tags of the present disclosure. Representative pore forming proteins include, but are not limited to, α-hemolysin, β-hemolysin, γ-hemolysin, aerolysin, cytolysin, leukocidin, melittin, MspA porin and porin A. The pore-forming protein, α-hemolysin from *Staphylococcus aureus* (also referred to herein as "α-HL"), is one of the most-studied members of the class of pore-forming proteins, and has been used extensively in creating nanopore devices. (See e.g., U.S. Publication Nos. 2015/0119259, 2014/0134616, 2013/0264207, and 2013/0244340.) α-HL also has been sequenced, cloned, extensively characterized structurally and functionally using a wide range of techniques including site-directed mutagenesis and chemical labelling (see e.g., Valeva et al. (2001), and references cited therein). It is contemplated that the compounds described herein can be used with α-HL heptameric nanopores that are formed from naturally occurring α-HL pore forming proteins, non-naturally occurring α-HL pore forming proteins, or combinations thereof. In one embodiment, the amino acid sequence of the naturally occurring (i.e., wild type) α-HL pore forming protein subunit is shown as SEQ ID NO: 22 (which is a mature sequence suitable for determining the location of substitutions described herein and therefore does not include the initial methionine residue). Non-naturally occurring α-HL pore forming proteins include, without limitation, variant pore polypeptides comprising one or more of the following substitutions: H35G, H144A, E111N, M113A, D127G, D128G, T129G, K131G, K147N, and V149K. Other suitable α-HL pore polypeptides are described in U.S. Published Patent Application Nos. 2017-0088588, as well as U.S. patent application Ser. Nos. 15/492,214, 15/274,770, and 15/638,273 each of which is hereby incorporated by reference herein.

A heptameric complex of α-HL monomers spontaneously forms a nanopore that embeds in and creates a pore through a lipid bilayer membrane. It has been shown that heptamers of α-HL comprising a ratio of 6:1 native α-HL to mutant α-HL can form nanopores (see e.g., Valeva et al. (2001) "Membrane insertion of the heptameric staphylococcal alpha-toxin pore—A domino-like structural transition that is allosterically modulated by the target cell membrane," *J. Biol. Chem.* 276(18): 14835-14841, and references cited therein). Further, α-HL has been engineered with cysteine residue substitutions inserted at numerous positions allowing for covalent modification of the protein through maleimide linker chemistry (Ibid.) For example, the engineered α-hemolysin-C46 ("α-HL-C46"), comprises a K46C amino acid residue substitution that allows for modification with a linker that can be used to covalently attach a strand-extending enzyme, such as polymerase, using common click reaction chemistry. Alternatively, the α-HL heptamer can be modified covalently with a DNA-polymerase using a Spy-Catcher/SpyTag conjugation method as described in WO 2015/148402, which is hereby incorporated by reference herein (see also, Zakeri and Howarth (2010), J. Am. Chem. Soc. 132:4526-7.

In one embodiment, the heptameric α-HL nanopore comprises at least one naturally occurring protein (i.e., wild type), and at least one non-naturally occurring protein. In another embodiment, the non-naturally occurring protein comprises an H144A amino acid substitution. In one other embodiment, the nanopore comprises one wild type protein and six proteins having the H144A substitution. In other embodiments, the non-naturally occurring protein comprises an H144A amino acid substitution and an H35G substitution. In some embodiments, the nanopore comprises one wild type protein and six proteins having the H144A and H35G substitution. In another embodiment, the heptameric α-HL nanopore comprises more than one non-naturally occurring protein. In one embodiment, the nanopore comprises a first and a second non-naturally occurring protein. In one other embodiment, the first non-naturally occurring protein comprises an H144A, an H35G, an E111N, an M113A, a K147N, a D127G, a D128G, a T129G, a K131G, and a V149K substitution. In another embodiment, the second non-naturally occurring protein comprises an E111N, an M113A, a K147N, a D127G, a D128G, a T129G, and a K131G substitution. In some embodiments, the nanopore comprises six of the first non-naturally occurring proteins and one of the first non-naturally occurring proteins.

Accordingly, in some embodiments, the ion flow amplifying tag compounds of the present disclosure can be used with a nanopore device, wherein the nanopore comprises a heptameric α-HL complex, which has 6:1 native α-HL to a modified, or an engineered version of α-HL, wherein the modified α-HL is conjugated covalently to a strand-extending enzyme, such as DNA polymerase. For example, the engineered α-HL-C46 can be modified with a linker allowing the use of tetrazine-trans-cyclooctene click chemistry to covalently attach a Bst2.0 variant of DNA polymerase to the heptameric 6:1 nanopore. Such an embodiment is described in U.S. Provisional Application No. 62/130,326, filed Mar. 9, 2015, and U.S. Published Patent Application No. 2017-0175183, each of which is hereby incorporated by reference herein.

The ion flow amplifying tagged nucleotides, associated compositions, and methods provided herein can be used with a wide range of strand-extending enzymes such as the polymerases and ligases known in the art.

DNA polymerases are a family of enzymes that use single-stranded DNA as a template to synthesize the complementary DNA strand. DNA polymerases add free nucleotides to the 3' end of a newly-forming strand resulting in extension of the new strand in the 5'-to-3' direction. Most DNA polymerases also possess exonucleolytic activity. For example, many DNA polymerases have 3'→5' exonuclease activity. Such multifunctional DNA polymerases can recognize an incorrectly incorporated nucleotide and use the 3'→5' exonuclease activity to excise the incorrect nucleotide, an activity known as proofreading. Following nucleotide excision, the polymerase can re-insert the correct nucleotide and strand extension can continue. Some DNA polymerases also have 5'→3' exonuclease activity.

DNA polymerases are used in many DNA sequencing technologies, including nanopore-based sequencing-by-synthesis. However, a DNA strand can move rapidly through the nanopore (e.g., at a rate of 1 to 5 μs per base), which can make nanopore detecting of each polymerase-catalyzed incorporation event difficult to measure and prone to high background noise, which can result in difficulties in obtaining single-nucleotide resolution. The ability to control the rate of DNA polymerase activity, as well as, increase the signal level from correct incorporation is important during sequencing-by-synthesis, particular when using nanopore detection. As shown in the Examples, the ion flow amplifying tagged nucleotide compounds of the present disclosure provide for a wider range of detectable tag current signals above the O.C. signal that provide better signal separation and lower noise levels, and thereby allow for more accurate nanopore-based nucleic acid detection and sequencing.

Exemplary polymerases that may be used with the ion flow amplifying tagged nucleotide compounds and methods of the present disclosure include the nucleic acid polymerases such as DNA polymerase (e.g., enzyme of class EC 2.7.7.7), RNA polymerase (e.g., enzyme of class EC 2.7.7.6 or EC 2.7.7.48), reverse transcriptase (e.g., enzyme of class EC 2.7.7.49), and DNA ligase (e.g., enzyme of class EC 6.5.1.1).

In some embodiments, the polymerase useful with ion flow amplifying tagged nucleotides is 9° N polymerase, E. coli DNA Polymerase I, Bacteriophage T4 DNA polymerase, Sequenase, Taq DNA polymerase, 9° N polymerase (exo-)A485L/Y409V or Phi29 DNA polymerase (φ29 DNA Polymerase).

In some embodiments, the strand extending enzyme that incorporates the ion flow amplifying tagged nucleotides comprises a DNA polymerase from *Bacillus stearothermophilus*. In some embodiments, the large fragment of DNA polymerase from *B. stearothermophilus*. In one embodiment, the polymerase is DNA polymerase Bst 2.0 (commercially available from New England BioLabs, Inc., Massachusetts, USA).

In some embodiments, the polymerase is a Pol6 DNA polymerase, or an exonuclease deficient variant of a Pol6, such as Pol6 having the mutation D44A. A range of additional Pol6 variants useful with the ion flow amplifying tagged nucleotides of the present disclosure are described in US patent publication no. 2016/0333327 A1, published Nov. 17, 2016, which is hereby incorporated by reference herein.

EXAMPLES

Various features and embodiments of the disclosure are illustrated in the following representative examples, which are intended to be illustrative, and not limiting. Those skilled in the art will readily appreciate that the specific examples are only illustrative of the invention as described more fully in the claims which follow thereafter. Every embodiment and feature described in the application should be understood to be interchangeable and combinable with every embodiment contained within.

Example 1: Preparation of Ion Flow Amplifying Tagged Nucleotide Compounds

This example illustrates a general method for preparation of a tagged nucleotide compound of structural formula (IIId), wherein the compound comprises nucleoside-5'-hexaphosphate, wherein the terminal phosphate group is linked to an ion flow amplifying tag comprising an oligonucleotide. More specifically, this example describes the preparation of the following three ion flow amplifying tagged nucleotide compounds shown in Table 6.

TABLE 6

| Tagged Nucleotide | Ion Flow Amplifying Tag (Sequence identifier) |
|---|---|
| dC6P-(Linker)[1]-TT-(dSp)$_{26}$-TT-C3 | -TT-(dSp)$_{26}$-TT-C3 (SEQ ID NO: 7) |
| dG6P-(Linker)[1]-TT-(SpC2)$_{28}$-biotin | -TT-(SpC2)$_{28}$-biotin (SEQ ID NO: 8) |
| dT6P-(Linker)[1]-TT-(SpC3)$_{28}$-biotin | -TT-(SpC3)$_{28}$-biotin (SEQ ID NO: 9) |

[1] "(Linker)" refers to the triazole linker of formula (XVd)

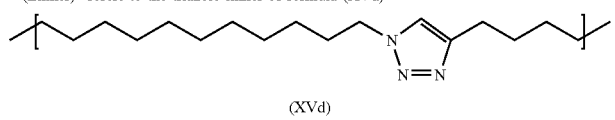

(XVd)

The synthesis method uses a standard Cu catalyzed azido-alkyne click reaction to covalently couple the 5'-end of an ion flow amplifying tag that is an oligonucleotide to the terminal phosphate group of the nucleotide hexaphosphate (dN6P) as shown generally in (1.84 g, 7.38 mmol) in anhydrous DMF (40 mL). The resulting white suspension was stirred under nitrogen atmosphere at ambient temperature overnight. The suspension was filtered and rinsed with DCM (50 mL). The solution was

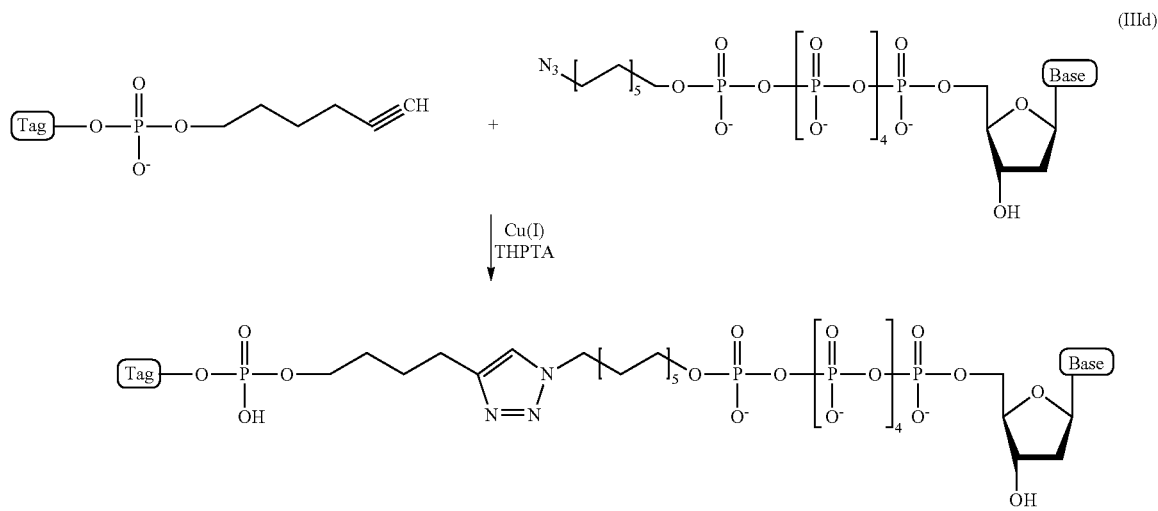

Scheme 2

This synthesis method of Scheme 2 is described below for the preparation of the specific ion flow amplifying tagged nucleotide, dT6P-(Linker)-TT-(SpC3)$_{28}$-biotin (i.e., compound of formula (IIIa), where Base is T and Tag is the oligonucleotide, TT-(SpC3)$_{28}$-biotin. This same method is used to prepare the other tagged nucleotides listed Table 6.

A. Synthesis dT6P-Azide (Compound (1))

concentrated under vacuum to give yellowish oil. The compound can be used in the following steps without further purification.

Preparation of 11-azido-1-undecanyl triphosphate 11-azido-1-undecanyl triphosphate is prepared according to the reaction Scheme 4 and procedure below.

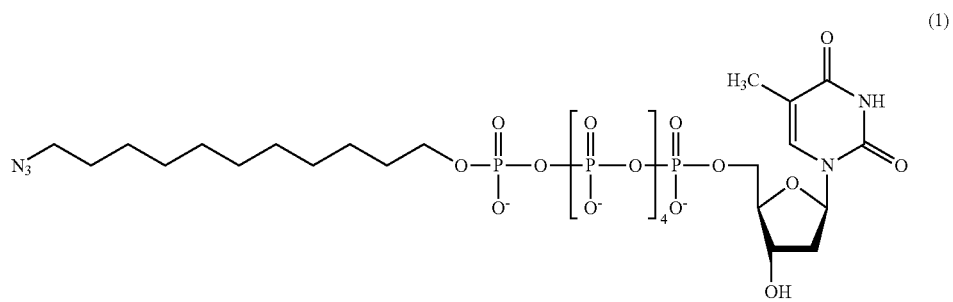

(1)

Preparation of 11-azido-1-undecanol 11-azido-1-undecanol is prepared according to the reaction Scheme 3 and procedure below.

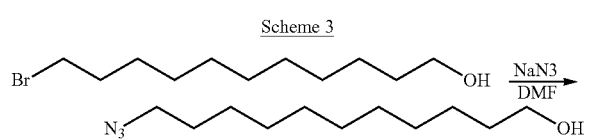

Scheme 3

Scheme 4

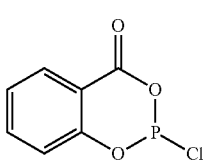

In a dried round bottom flask, sodium azide (1.44 g, 22 mM) was added to a solution of 11-Bromo-1-undecanol -continued

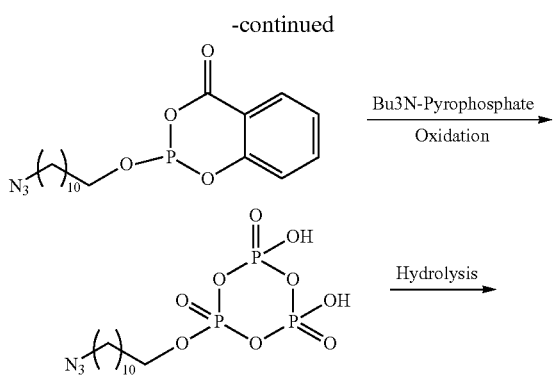

Preparation of dT6P-azide (Compound (1))

dT6P-azide is prepared according to the reaction Scheme 5 and procedure below.

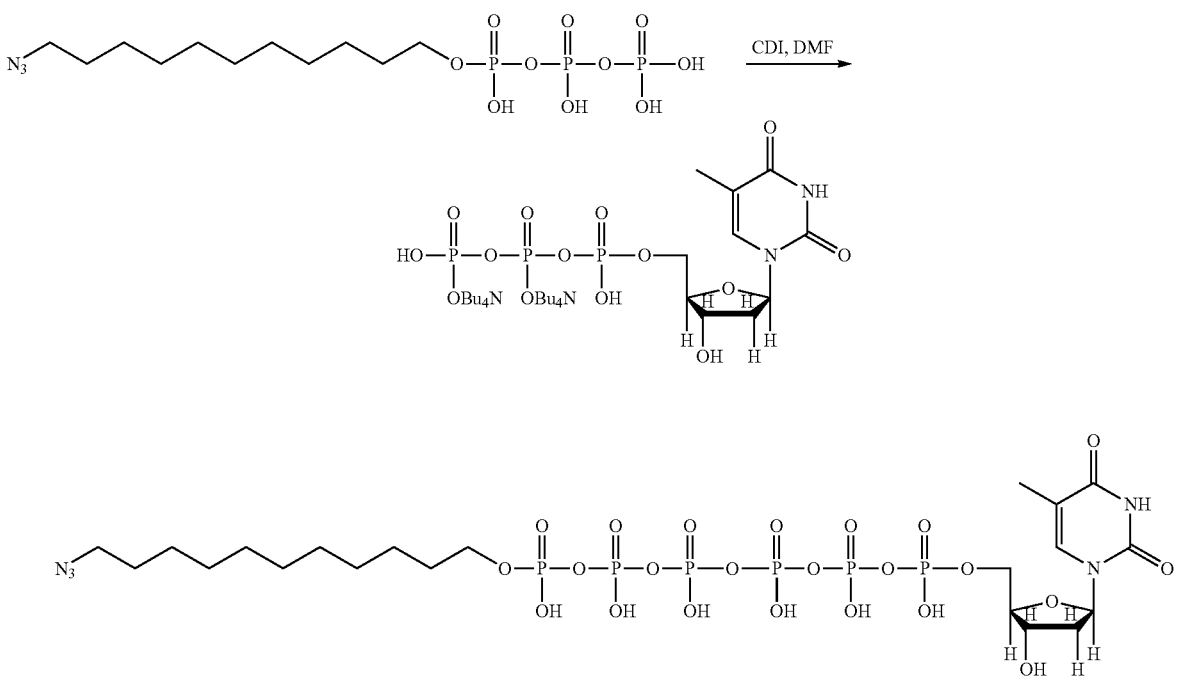

-continued

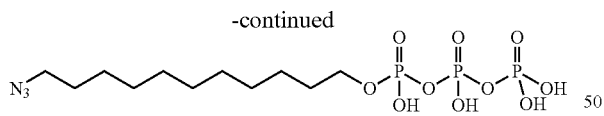

In a dried round bottom flask, 11-azido-1-undecanol (0.20 g, 0.94 mmol) was dissolved in anhydrous DMF (2.0 mL). Salicyl chlorophosphite (0.20 g, 1.03 mmol) was added in one portion. The resulting solution was stirred at ambient temperature under nitrogen for 45 minutes. In another flask, a solution of pyrophosphate tributylamine (0.566, 1.03 mmol) in anhydrous DMF and tributylamine (1.39 g, 7.51 mmol) was prepared and then added to the reaction solution. The resulting mixture was stirred for an hour and was oxidized with 20 mM iodine solution (80 mL, 1.55 mmol), giving cyclic meta-triphosphate intermediate that can be analyzed by mass spectrometer. After another hour of stirring, the reaction was quenched first with $Na_2SO_3$ (10%, 4 mL), allowed to stir for 20 minutes, followed by TEAB (0.10 M, 20 mL). The resulting mixture was stirred at ambient temperature overnight. The crude product was purified by TeleDyne CombiFlash RF+column system using 30 g HP C18 column eluting with $CH_3CN/0.1$ TEAA (0%/o to 50% $CH_3CN$ in 16 minutes). The product is concentrated under vacuum and dried on a lyophilizer.

11-azido-1-undecanyl triphosphate (0.091 g, 0.12 mmol) was dissolved in anhydrous DMF (1.5 mL) and was activated with carbonyl diimidazole ("CDI") (0.078 g, 0.48 mmol) for 4 hours at ambient temperature. The excess CDI was quenched with methanol (0.029 mL, 0.72 mmol), stirring additional 30 minutes. Then a solution of dTTP+3Bu4N (0.20 g, 0.17 mmol) in anhydrous DMF (2.0 mL) was added, followed by $MgCl_2$ (0.114 g, 1.20 mmol). The resulting slurry solution was stirred for 24-36 hours at ambient temperature. The reaction was quenched with TEAB 0.1 M (20 mL), stirring for 30 minutes. The crude compound (1) was purified by ion-exchange chromatography (0.1 M to 1 M in 30 minutes), followed by RP-C18 HPLC (10-45% $CH_3CN$ in 35 minutes) to yield 15-30 μmol of product. The formation of the compound (1) was confirmed by mass spectrometry (cal. 917.06, observed 916.03 for negative ion).

B. Synthesis of 5'-propargyl-TT-(Sp3)$_{28}$-biotin oligonucleotide (Compound (2))

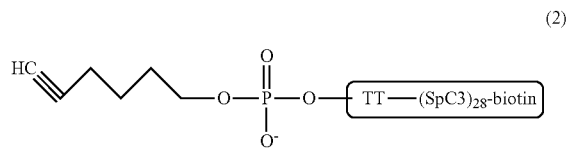

(2)

The 5'-propargyl-TT-(SpC3)$_{28}$-biotin oligonucleotide used as a tag was synthesized on an ABI 3900 DNA Synthesizer using standard solid phase phosphoramidite chemistry protocols and commercially available reagents, including the abasic 3 carbon spacer amidite, "SpC3," and the biotin amidite reagents (available from e.g., Glen Research, 22825 Davis Drive, Sterling, Va., USA). In the final automated oligonucleotide synthesis step a propargyl-C$_5$-phosphoramidite linker was added to the 5'-phosphate of the penultimate T nucleotide resulting in the propargyl-modified oligonucleotide of compound (2).

C. Click-Reaction to Form Tagged Nucleotide, dT6P-(Linker)-TT-(SpC3)$_{28}$-biotin The click reaction forming ion flow amplifying tagged nucleotide compound, dT6P-(Linker)-TT-(SpC3)$_{28}$-biotin is carried out according to the reaction of Scheme 2 and the following procedures. The dT6P-azide (compound (1)) (300 nmol) and the 5'-propargyl-TT-(Sp3)$_{28}$-biotin oligonucleotide (compound (2)) (100 nmol) are mixed in DI-water (100 µL). The copper-catalyzed azido-alkyne click-reaction is initiated according to the standard literature procedure using Cu(I) bromide (6000 nmol) and THPTA (4000 nmol) in a mixture solution of DMSO/t-Butanol (3:1). The reaction solution is mixed at ambient temperature overnight on a shaker. The crude mixture is purified by RP C18-HPLC (0.1M TEAA/CH$_3$CN). Formation of the desired conjugated product, dT6P-(Linker)-TT-(SpC3)$_{28}$-biotin, is confirmed by mass spectrometer (MS calc. 5939.8; MS obsd. 5940.9 for negative ion).

Formation of the other two tagged nucleotides of Table 6 are also confirmed by mass spectrometer as follows: dC6P-(Linker)-TT-(dSp)$_{26}$-TT-C3 (MS calc. 7037.7; MS obsd. 7038.0 for negative ion); dG6P-(Linker)-TT-(SpC2)$_{28}$-biotin (MS calc. 5571.9; MS obsd. 5573.0 for negative ion).

Example 2: Use of Ion Flow Amplifying Tagged Nucleotides for Nanopore Sequencing This example illustrates the improved nanopore detection characteristics of a set of four different tagged nucleotide compounds (shown in Table 7) corresponding to each of the four canonical nucleotides, A, C, T, and G, which can be incorporated by a polymerase.

TABLE 7

| Tagged Nucleotides | Oligonucleotide Tag |
|---|---|
| dA6P-(Linker)-T$_{30}$-C3 | SEQ ID NO: 10 |
| dC6P-(Linker)-TT-(dSp)$_{26}$-TT-C3 | SEQ ID NO: 7 |

TABLE 7-continued

| Tagged Nucleotides | Oligonucleotide Tag |
|---|---|
| dG6P-(Linker)-TT-(SpC2)$_{28}$-biotin | SEQ ID NO: 8 |
| dT6P-(Linker)-TT-(SpC3)$_{28}$-biotin | SEQ ID NO: 9 |

Abbreviations are those commonly used for oligonucleotide synthesis: "dSp" = abasic furan spacer; "SpC2" = abasic 2 carbon spacer; "SpC3" = abasic 3 carbon spacer; "C3" = 3'-propanol.
"(Linker)" refers to the triazole linker of formula (XVd).

In the set, the nucleotide hexaphosphate compounds, dC6P, dG6P, and dT6P, each is tagged with a different ion-flow enhancing tag. Each of these three comprises a negatively-charged polymer of 30 phosphodiester-linked monomer units (i.e., an oligonucleotide) covalently coupled to the terminal phosphate of the nucleotide hexaphosphate via a triazole linker formed as described in Example 1. The fourth tagged nucleotide hexaphosphate in the set is a dA6P tagged with a T$_{30}$-C3 oligonucleotide. This tagged nucleotide is known to not result in increased ion flow through a nanopore but rather results in a blocking current below O.C. indicated decreased ion flow.

Briefly, the nanopore detection of the set of four tagged nucleotides is carried out using an array of α-HL nanopores each conjugated to Pol6 polymerase. The α-HL-Pol6 nanopore conjugates are embedded in membranes formed over an array of individually addressable integrated circuit chips. This α-HL-Pol6 nanopore array is exposed to a DNA template and a set of the three different nucleotide substrates tagged with different ion-flow enhancing tags shown in Table 7. As the specific tagged nucleotide that is complementary to the DNA template is captured and bound to the Pol6 polymerase active site, the ion-flow enhancing tag moiety becomes positioned in the α-HL nanopore conjugated nearby. Under the applied AC potential, the presence of the tag in the pore causes an increase in positive ion flow through the nanopore resulting in a distinctive current measured at the nanopore device electrodes that is greater than the O.C. current (i.e., current with no tag in the nanopore). The distinctive above-O.C. currents measured as the different tag moieties enter the nanopore during Pol6 synthesis of a complementary DNA extension strand can be used to detect and identify the DNA template.

Nanopore Detection System:

The nanopore ion-flow measurements are performed using a nanopore array microchip comprising a CMOS microchip that has an array of 128,000 silver electrodes within shallow wells (chip fabricated by Genia Technologies, Mountain View, Calif., USA). Methods for fabricating and using such nanopore array microchips can also be found in U.S. Patent Application Publication Nos. 2013/0244340 A1, US 2013/0264207 A1, and US2014/0134616 A1 each of which is hereby incorporated by reference herein. Each well in the array is manufactured using a standard CMOS process with surface modifications that allow for constant contact with biological reagents and conductive salts. Each well can support a phospholipid bilayer membrane with a nanopore-polymerase conjugate embedded therein. The electrode at each well is individually addressable by computer interface. All reagents used are introduced into a simple flow cell above the array microchip using a computer-controlled syringe pump. The chip supports analog to digital conversion and reports electrical measurements from all electrodes independently at a rate of over 1000 points per second. Nanopore blocking current measurements can be made asynchronously at each of 128K addressable nanoporecontaining membranes in the array at least once every millisecond (msec) and recorded on the interfaced computer.

Formation of Lipid Bilayer on Chip:

The phospholipid bilayer membrane on the chip is prepared using 1,2-diphytanoyl-sn-glycero-3-phosphocholine (Avanti Polar Lipids). The lipid powder is dissolved in decane at 15 mM and then painted in a layer across the wells on the chip. A thinning process then is initiated by pumping air through the ds side of the array wells, thus reducing multi-lamellar lipid membranes to a single bilayer.

Insertion of α-HL-Pol6 conjugate in membrane: After the lipid bilayer forms on the wells of the array chip, 0.1 µM of a 6:1 α-HL-Pol6 nanopore-polymerase conjugate, 0.4 µM of the desired DNA template, all in a buffer solution of 3 mM $MgCl_2$, 20 mM HEPES, and 300 mM K-Glu, pH 8, at 20° C. is added to the cis side of the chip. The nanopore-polymerase conjugate in the mixture either is electroporated or spontaneously inserts into the lipid bilayer. The non-polymerase modified α-HL nanopores (i.e., the 6 subunits of the 6:1 heptamer) include the H144A mutation.

The DNA template is a dumb-bell circular template which has the sequence:

```
                                       (SEQ ID NO: 11)
CAGTCAGTAGAGAGAGATATCTCTCTCAAAAACGGAGGAGGAGGACAGTC
AGTAGAGAGAGATATCTCTCTCAAAAACGGAGGAGGAGGA.
```

Nanopore Ion Flow Measurements:

After insertion of the complex into the membrane, the solution on the cis side is replaced by 300 mM potassium glutamate, pH 8, 3 mM $MgCl_2$, 10 mM LiCl, 20 mM HEPES, 5 mM TCEP, 10 µM of the set of the 4 differently tagged nucleotides (3 of which are tagged with different ion-flow enhancing tags), 10 µM of the one nucleotide tagged with ion blocking tag, at 20° C. The trans side buffer solution is: 380 mM potassium glutamate, 3 mM $MgCl_2$, 10 mM LiCl, 20 mM HEPES, pH 8. These buffer solutions are used as the electrolyte solutions for the nanopore ion flow measurements. A Pt/Ag/AgCl electrode setup is used and an AC current of a −10 mV to 200 mV square waveform applied at 50 Hz. AC current has certain advantages for nanopore detection as it allows for the tag to be repeatedly directed into and then expelled from the nanopore thereby providing more opportunities to measure signals resulting from the ion flow through the nanopore. Also, the ion flow during the positive and negative AC current cycles counteract each other to reduce the net rate of ion depletion from the cis side, and possible detrimental effects on signals resulting from this depletion.

Tag current signals representing four distinct ion-flow events are observed from the set of four tagged nucleotides as they are captured by the α-HL-Pol6 nanopore-polymerase conjugates primed with the DNA template. Plots of these events are recorded over time and analyzed. Generally, events that last longer than 10 ms indicate productive nucleotide capture coincident with polymerase incorporation of the correct base complementary to the template strand.

Results

As shown in FIG. 1, signals representing three distinct ion-flow enhancement events and an ion-flow blocking event are observed from the set of four tagged nucleotides as they are captured by the α-HL-Pol6 nanopore-polymerase conjugates primed with the DNA template. Average tag current values measure for relevant nanopore array carried out with the set of tagged nucleotides are shown in Table 8.

TABLE 8

| Tagged Nucleotide | Tag Current (% O.C.) |
|---|---|
| dA6P-(Linker)-$T_{30}$-C3 | 50 |
| dC6P-(Linker)-TT-$(dSp)_{26}$-TT-C3 | 125 |
| dG6P-(Linker)-TT-$(SpC2)_{28}$-biotin | 175 |
| dT6P-(Linker)-TT-$(SpC3)_{28}$-biotin | 150 |

"(Linker)" refers to the triazole linker of formula (XVd).

As shown by plot of FIG. 1 and the results in Table 8, the three ion flow amplifying tagged nucleotides (dC6P-(Linker)-TT-$(dSp)_{26}$-TT-C3; dT6P-(Linker)-TT-$(SpC3)_{28}$-biotin; and dG6P-(Linker)-TT-$(SpC2)_{28}$-biotin) exhibit tag current signal levels above the open channel current of the nanopore indicating that the presence of the tag in the nanopore results in increase positive ion flow. The fourth tagged nucleotide present, dA6P-(Linker)-$T_{30}$-C3, exhibits a tag current signal level below open channel current (i.e., a blocking current) indicating the presence of the tag in the nanopore results in decreased positive ion flow through the nanopore. The ability to provide tag currents signals above open channel provides a wider dynamic range for nanopore detection of tags. The wide range and broad separation between the ion flow events resulting from this set of tags allows for more accuracy in detecting and/or sequencing nucleic acids using nanopore devices.

Example 3: Ion Flow Amplifying Tagged Nucleotides

Nanopore detection experiments can be used to identify additional tagged nucleotide compounds which have ion flow amplifying characteristics that allow for detection above open channel.

Nanopore detection experiments carried out according to the general methods described in Example 2 identified the tagged nucleotides shown in Table 9. These tagged nucleotides can be incorporated by a polymerase and provide a tag current signal above open channel.

TABLE 9

| Tagged Nucleotide | Tag Sequence (SEQ ID NO:) | Tag Current (% O.C.) |
|---|---|---|
| dG6P-(Linker)-(SpC2)$_8$-T$_6$-(SpC2)$_{16}$-C3 | 17 | 120[1] |
| dC6P-(Linker)-(SpC2)$_8$-(N3CEdT)$_7$-(SpC2)$_{15}$-C3 | 18 | 120[2] |
| dA6P-(Linker)-(SpC2)$_6$-TT-(BHEB)-T-(SpC2)$_{20}$-C3 | 19 | 155[1] |
| dC6P-(Linker)-(SpC2)$_9$-T-(BHEB)$_2$-T-(SpC2)$_{17}$-C3 | 20 | 189[1] |
| dT6P-(Linker)-(SpC2)$_8$-(S500)$_3$-(SpC2)$_{17}$-C3 | 21 | 170[2] |

[1] Cis side buffer solution: 300 mM K-Glu, 10 mM MgCl$_2$, 15 mM LiCl, 20 mM HEPES, pH 8; trans side buffer solution: 380 mM K-Glu, 5 mM MgCl$_2$, 15 mM LiCl, 5 mM TCEP, 20 mM HEPES, pH 8; AC current: 10 to 140 mV at 50 Hz.
[2] Cis side buffer solution: 300 mM K-Glu, 10 mM MgCl$_2$, 15 mM LiOAc, 5 mM TCEP, 20 mM HEPES, pH 7.8; trans side buffer solution: 380 mM K-Glu, 10 mM MgCl$_2$, 15 mM LiOAc, 20 mM HEPES, pH 7.5; AC current: 10 to 140 mV at 50 Hz.

Abbreviations:
"dSp" = abasic furan spacer;
"SpC2" = abasic 2 carbon spacer;
"SpC3" = abasic 3 carbon spacer;
"N3CET" = 3-N-cyanoethyl-dT amidite (dT with a cyanoethyl group at position N3 of the base);
"BHEB" = bis-hydroxyethylbenzene, which is a spacer that provides the following 1,4-bis-ethyl-benzene phosphodiester structure in an oligonucleotide:

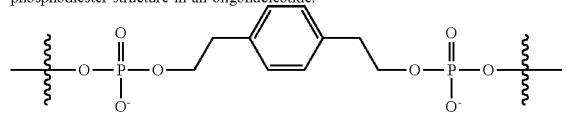

"S500" = 1,4-bis(3-butyn-1-ol)benzene, which is a spacer that provides the following 1,4-bis-butyn-benzene phosphodiester structure in an oligonucleotide:

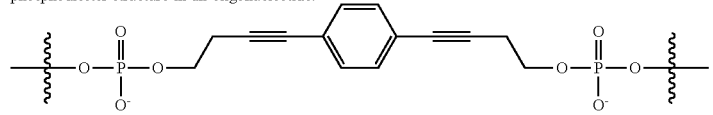

"C3" = 3'-propanol;
"(Linker)" refers to the triazole linker of formula (XVd).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A compound of structural formula (I)

N-P-L-T   (I)

wherein,
  N is a nucleoside;
  P is an oligophosphate covalently attached to a 5'-O group of the nucleoside, wherein the oligophosphate consists of 3 to 12 phosphate groups;
  L is a linker covalently attached to a terminal phosphate group of the oligophosphate; and
  T is a tag covalently attached to the linker, wherein the tag comprises a negatively-charged polymer moiety which is capable of entering a nanopore and upon entering a nanopore in the presence of positive ions results in an increased flow of the positive ions through the nanopore, wherein the negatively-charged polymer moiety comprises a covalently linked chain of from 20 to 50 monomer units selected from the monomer unit structures of formula (1a), (1b), (1c), (1d), (1e), (1f), (1g), (1h), (1i), (1j), (1k), (1l), (1m), and any combinations thereof

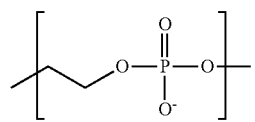  (1a)

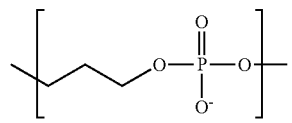  (1b)

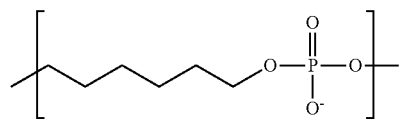  (1c)

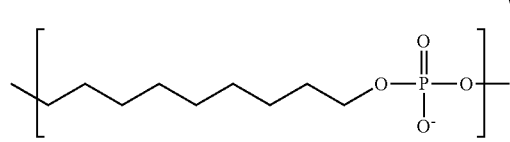  (1d)

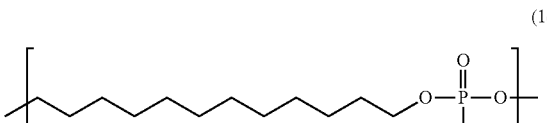  (1e)

  (1f)

  (1g)

  (1h)

  (1i)

  (1j)

  (1k)

  (1l)

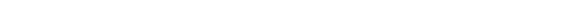  (1m)

2. The compound of claim 1, wherein the compound has a structural formula (II)

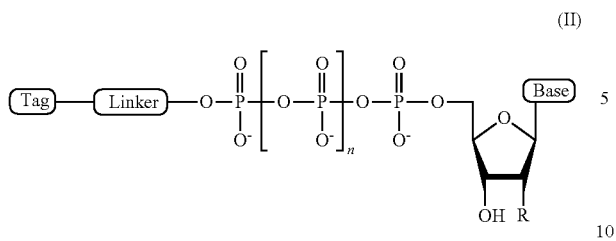

(II)

wherein,
Base is selected from adenosine, cytidine, guanosine, thymidine, and uridine;
R is selected from H and OH;
n is from 1 to 4;
Linker is a linker comprising a covalently bonded chain of 2 to 100 atoms; and
Tag is the tag comprising the negatively-charged polymer moiety.

3. The compound of claim 2, wherein the linker comprises a chemical group selected from the group consisting of: ester, ether, thioether, amine, amide, imide, carbonate, carbamate, squarate, thiazole, thiazolidine, hydrazone, oxime, triazole, dihydropyridazine, phosphodiester, polyethylene glycol (PEG), and any combination thereof.

4. The compound of claim 1, wherein the compound has a structural formula (III)

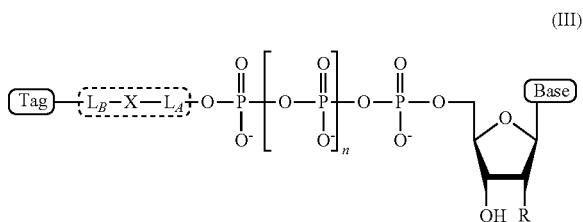

(III)

wherein,
Base is selected from adenosine, cytidine, guanosine, thymidine, and uridine;
R is selected from H and OH;
n is from 1 to 4;
$L_B$-X-$L_A$ is the linker, wherein (a) $L_A$ and $L_B$ each independently comprises a chemical moiety selected from the group consisting of: linear ($C_1$-$C_{12}$) alkyl, linear ($C_1$-$C_{12}$) alkene, linear ($C_1$-$C_{12}$) alkyne, ester, ether, thioether, amine, amide, imide, carbonate, carbamate, squarate, thiazole, thiazolidine, hydrazone, oxime, triazole, dihydropyridazine, phosphodiester, polyethylene glycol (PEG), and combinations thereof; and (b) X comprises a chemical moiety selected from the group consisting of ester, ether, thioether, amine, amide, imide, carbonate, carbamate, squarate, thiazole, thiazolidine, hydrazone, oxime, triazole, and dihydropyridazine; and Tag is the tag comprising the negatively-charged polymer moiety.

5. The compound of claim 4, wherein the compound has a structural formula (IIIa)

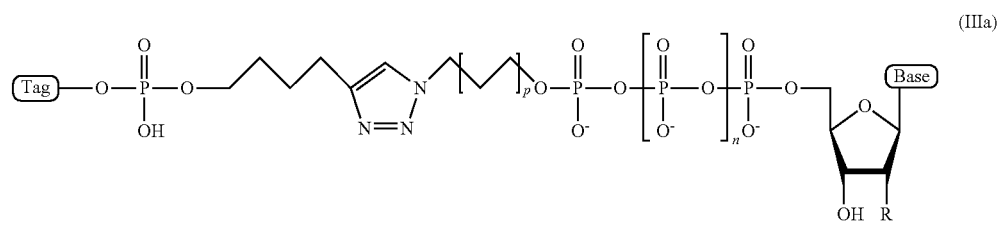

(IIIa)

wherein,
Base is selected from adenosine, cytidine, guanosine, thymidine, and uridine;
R is selected from H and OH;
n is from 1 to 4;
p is from 2 to 10; and
Tag is the tag comprising the negatively-charged polymer moiety.

6. The compound of claim 5, wherein R=H, n=4, and p=5.

7. The compound of claim 1, wherein the increased ion flow results in a measured current across the nanopore that is greater than O.C. current, optionally at least 5% greater than O.C. current, at least 10% greater than O.C. current, at least 25% greater than O.C. current, or at least 50% greater than O.C. current.

8. The compound of claim 1, wherein the negatively-charged polymer moiety has an overall negative charge of from (−25) to (−50), optionally an overall negative charge of from (−30) to (−40), or optionally an overall negative charge of from (−31) to (−37).

9. The compound of claim 1, wherein the negatively-charged polymer moiety comprises a covalently linked chain of from 25 to 40 monomer units.

10. The compound of claim 1, wherein the negatively-charged polymer moiety comprises a formula (A)m-(B)n-(C)p-(D)q, wherein A, B, C, and D, are monomer units independently selected from the monomer unit structures of formula (1a), (1b), (1c), (1d), (1e), (1f), (1g), (1h), (1i), (1j), (1k), (1l), and (1m), and each of m, n, p, and q is from 0 to 40, and m+n+p+q is from 20 to 40.

11. The compound of claim 1, wherein the negatively-charged polymer moiety is selected from the group consisting of: -TF-(SpC2)$_{28}$- (SEQ ID NO: 1), -TT-(SpC3)$_{28}$- (SEQ ID NO: 2), -(SpC3)$_{31}$- (SEQ ID NO: 3), -TT-(dSp)$_{26}$-TT- (SEQ ID NO: 4), -TF-(SpC4-F4)$_{28}$- (SEQ ID NO: 5), -TT-(SpC7-Pra2)$_{28}$- (SEQ ID NO: 6), -(SpC2)$_8$-T$_6$-(SpC2)$_{16}$- (SEQ ID NO: 12), -(SpC2)$_8$-(N3CEdT)$_7$-(SpC2)$_{15}$- (SEQ ID NO: 13), -(SpC2)$_6$-TT-(BHEB)-T-(SpC2)$_{20}$-(SEQ ID NO: 14), -(SpC2)$_9$-T-(BHEB)$_2$-T-(SpC2)$_{17}$- (SEQ ID NO: 15), and -(SpC2)$_8$-(S500)$_3$-(SpC2)$_{17}$- (SEQ ID NO: 16).

12. A composition comprising a set of compounds, each compound of the set comprising a different tag which results in a different flow of positive ions through a nanopore when the tag enters the nanopore, wherein at least one of the compounds of the set is a compound according to claim 1.

* * * * *